(12) United States Patent
Nanaumi et al.

(10) Patent No.: US 10,064,557 B2
(45) Date of Patent: Sep. 4, 2018

(54) APPARATUS FOR ACQUIRING PROPERTY INFORMATION ON THE INTERIOR OF AN OBJECT BASED ON AN ACOUSTIC WAVE GENERATED FROM THE OBJECT IRRADIATED WITH LIGHT

(71) Applicant: CANON KABUSHIKI KAISHA, Tokyo (JP)

(72) Inventors: Ryuichi Nanaumi, Tokyo (JP); Takuro Miyasato, Tokyo (JP); Kazuhiko Fukutani, Yokohama (JP); Yoshiko Nakamura, Kyoto (JP); Takuji Oishi, Kawasaki (JP); Hiroshi Abe, Kyoto (JP); Kohtaro Umezawa, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 73 days.

(21) Appl. No.: 14/970,698

(22) Filed: Dec. 16, 2015

(65) Prior Publication Data

US 2016/0189375 A1 Jun. 30, 2016

(30) Foreign Application Priority Data

Dec. 25, 2014 (JP) ................................. 2014-262967

(51) Int. Cl.
*G06K 9/00* (2006.01)
*A61B 5/00* (2006.01)

(52) U.S. Cl.
CPC .................................. *A61B 5/0095* (2013.01)

(58) Field of Classification Search
None
See application file for complete search history.

(56) References Cited

U.S. PATENT DOCUMENTS

| 5,762,067 | A  | * | 6/1998  | Dunham ............. | A61B 1/0052 600/148 |
| 8,144,327 | B2 |   | 3/2012  | Nakajima et al. ............ | 356/432 |
| 2009/0131798 | A1 | * | 5/2009 | Minar ................ | A61B 5/02007 600/463 |
| 2010/0174197 | A1 |   | 7/2010 | Nakajima et al. ............ | 600/478 |
| 2011/0208057 | A1 | * | 8/2011 | Oikawa ................ | A61B 5/0095 600/443 |
| 2011/0275890 | A1 | * | 11/2011 | Wang ................... | A61B 5/0062 600/104 |

(Continued)

OTHER PUBLICATIONS

M. Xu et al., "Analytic explanation of spatial resolution related to bandwidth and detector aperture size in thermoacoustic or photoacoustic reconstruction", Physical Review E, vol. 67, pp. 056605-1 to 056605-15 (May 9, 2003).

(Continued)

*Primary Examiner* — Tahmina Ansari
(74) *Attorney, Agent, or Firm* — Fitzpatrick, Cella, Harper & Scinto

(57) ABSTRACT

An object information acquiring apparatus, includes: an irradiator irradiating an object with light; a probe having a plurality of transducers which receive an acoustic wave generated from the object irradiated with the light and output a reception signal; and a controller using the reception signal to acquire property information on the interior of the object, and the probe has a plurality of apertures and a surface on which the plurality of transducers are arranged has a spherical surface shape.

15 Claims, 21 Drawing Sheets

(56) References Cited

U.S. PATENT DOCUMENTS

2013/0165795 A1* 6/2013 Nakabayashi ......... A61B 8/406
 600/459
2016/0189375 A1* 6/2016 Nanaumi ............. A61B 5/0095
 382/128

OTHER PUBLICATIONS

U.S. Appl. No. 14/967,497, filed Dec. 14, 2015.

* cited by examiner

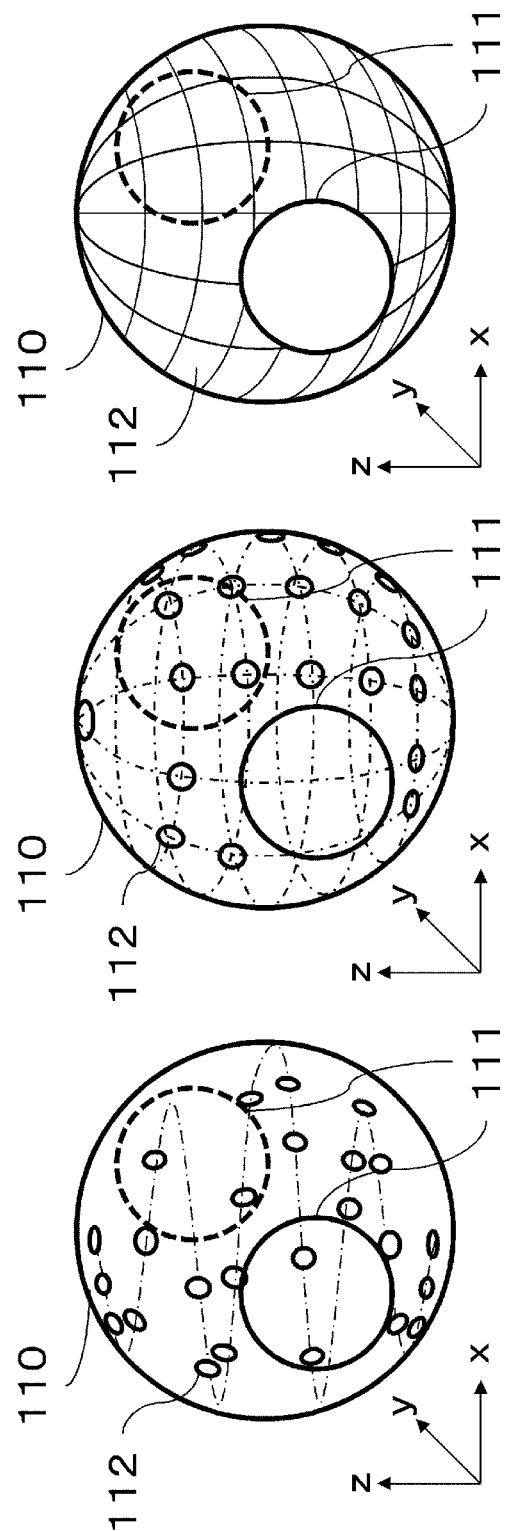

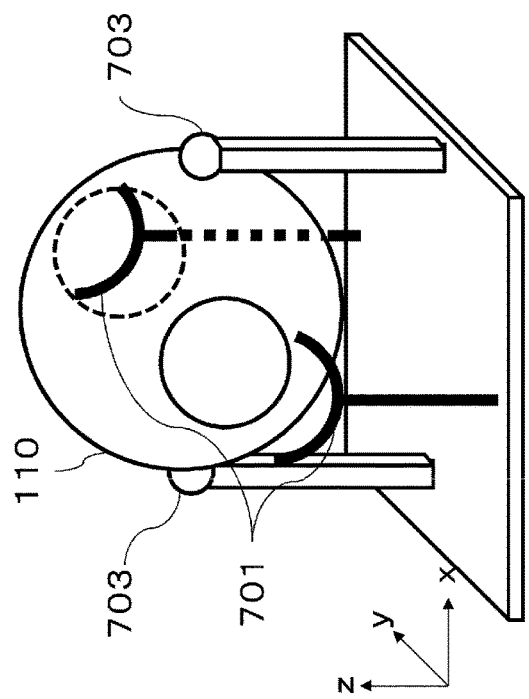
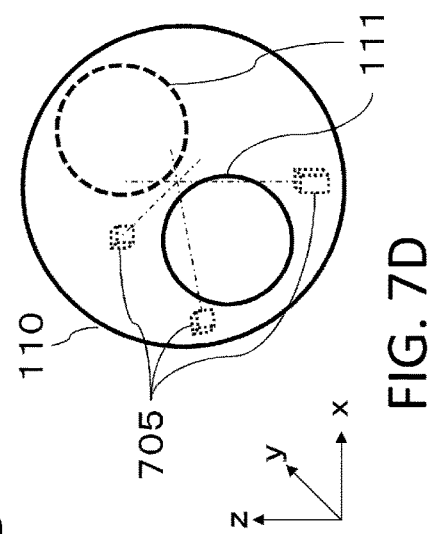
FIG. 7A
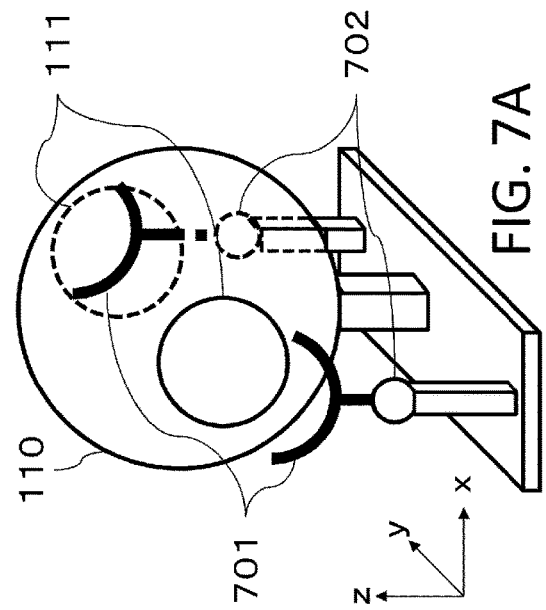
FIG. 7B
FIG. 7C
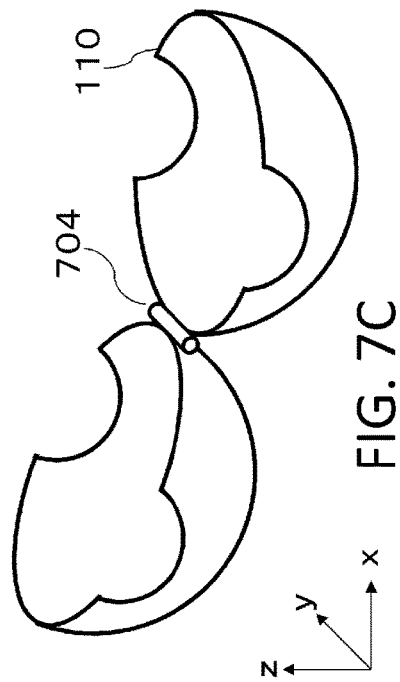
FIG. 7D

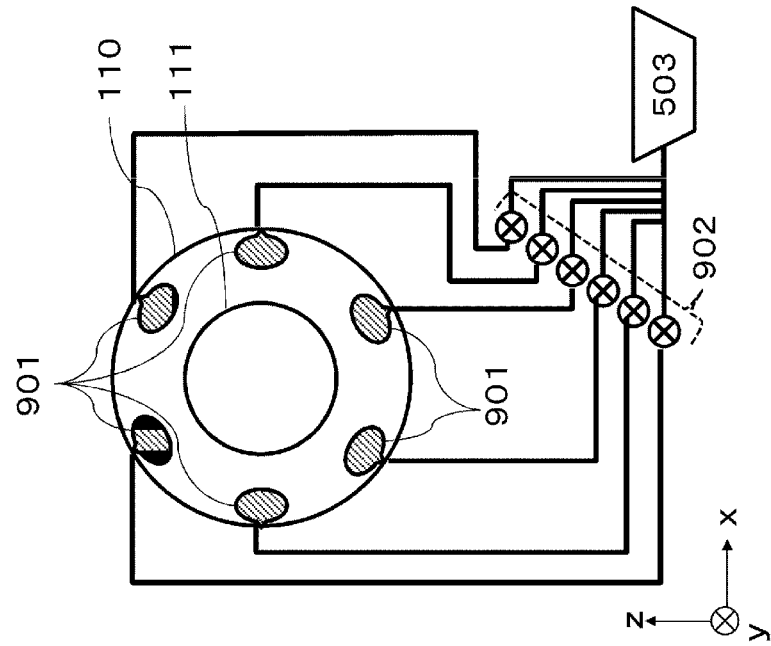
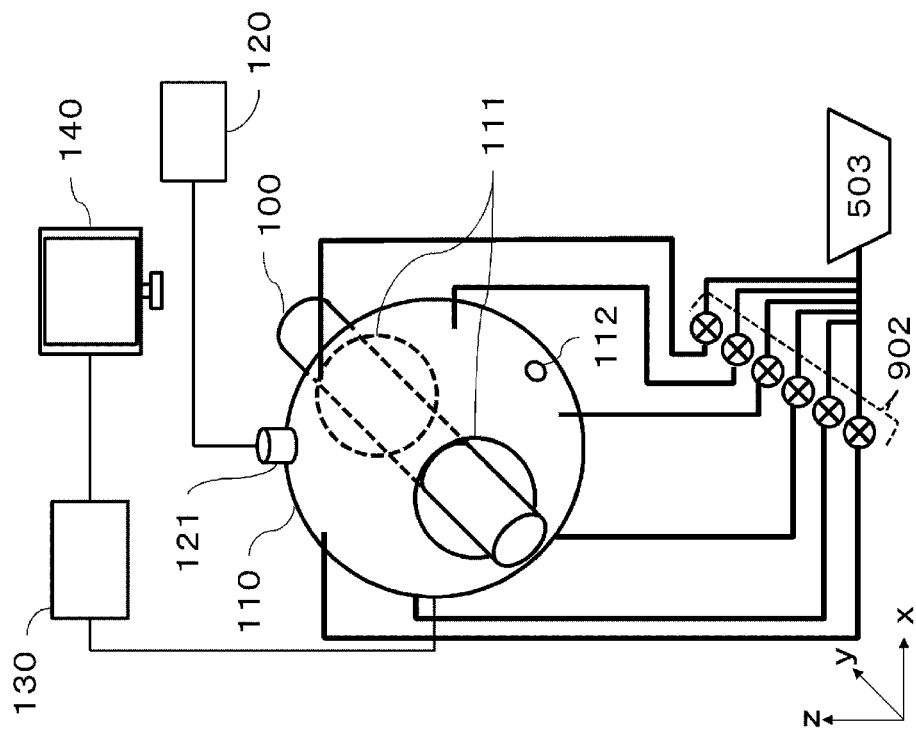
FIG. 9A
FIG. 9B

APPARATUS FOR ACQUIRING PROPERTY INFORMATION ON THE INTERIOR OF AN OBJECT BASED ON AN ACOUSTIC WAVE GENERATED FROM THE OBJECT IRRADIATED WITH LIGHT

BACKGROUND OF THE INVENTION

Field of the Invention

The present invention relates to an object information acquiring apparatus.

Description of the Related Art

Conventionally, an object information acquiring apparatus, such as a photoacoustic imaging apparatus and ultrasound echo imaging apparatus, has been proposed as technology for acquiring information on the interior of an object, such as a living body, by receiving acoustic waves. Photoacoustic imaging apparatuses are used widely, particularly in the diagnosis of skin cancer and breast cancer, and are expected to replace conventionally used devices, such as ultrasound echo diagnostic apparatuses, X-ray apparatuses, MRI apparatuses, and so on.

When a living body tissue is irradiated with measurement light, such as visible light or near-infrared light, the light absorbing material in the living body, for example, material such as hemoglobin in blood, absorbs the energy of the measurement light and momentarily swells, giving rise to an acoustic wave. This phenomenon is called the photoacoustic effect, and the acoustic wave generated thereby is called a photoacoustic wave. Photoacoustic imaging (PAI) is a technology which makes information about living body tissue visible by measuring this photoacoustic wave. A technique of cross-sectional imaging using photoacoustic waves is called "photoacoustic tomography (PAT)".

In photoacoustic imaging, information relating to the absorption coefficient of the interior of an object can be converted into an image. The absorption coefficient is the ratio at which the living body tissue absorbs light energy. The information related to the absorption coefficient is, for example, the initial sound pressure, which is the sound pressure at the moment that the photoacoustic wave is generated. The initial sound pressure is directly proportional to the product of the light energy (light intensity) and absorption coefficient. Consequently, it is possible to acquire the absorption coefficient by carrying out suitable processing on the value of the initial sound pressure.

Moreover, the absorption coefficient is dependent on the concentration of the components which constitute the living body tissue. Therefore, it is possible to acquire the concentration of the constituent components from the absorption coefficient. In particular, it is possible to acquire the density ratio of oxygenated hemoglobin and reduced hemoglobin and the oxygen saturation of the living body tissue, by using light of a wavelength that can be absorbed readily by hemoglobin in the blood. By analyzing the oxygen saturation distribution, application to medical diagnosis, such as determination of tumor tissue and peripheral tissue inside the living body, is expected.

"Minghua Xu and Lihong V. Wang, "Analytic explanation of spatial resolution related to bandwidth and detector aperture size in thermoacoustic or photoacoustic reconstruction", PHYSICAL REVIEW E 67, 056605 (2003)" discloses an ultrasound wave probe having a round cylindrical surface shape. Furthermore, the resolution of the photoacoustic imaging is indicated for respective probe shapes, such as a flat surface, cylindrical surface and spherical surface. Moreover, it has been disclosed that a high-resolution region is located near the center of curvature of a spherical surface-shaped probe.

Non Patent Literature 1: Minghua Xu and Lihong V. Wang, "Analytic explanation of spatial resolution related to bandwidth and detector aperture size in thermoacoustic or photoacoustic reconstruction", PHYSICAL REVIEW E 67, 056605 (2003)

SUMMARY OF THE INVENTION

In photoacoustic imaging, in order to accurately ascertain the state of the object, there have been demands to acquire property information for the object at high resolution. Furthermore, there are cases where the resolution differs according to the type of various probes, as disclosed in "Minghua Xu and Lihong V. Wang, "Analytic explanation of spatial resolution related to bandwidth and detector aperture size in thermoacoustic or photoacoustic reconstruction", PHYSICAL REVIEW E 67, 056605 (2003)", and there is a possibility of countermeasures being necessary.

The present invention was devised in view of the abovementioned problem, an object thereof being to provide technology for raising the resolution when determining property information on the object.

The present invention provides an object information acquiring apparatus, comprising:

an irradiator configured to irradiate an object with light;

a probe including a plurality of transducers configured to output a reception signal by receiving an acoustic wave generated from the object irradiated with the light; and a controller configured to acquire property information on the interior of the object by using the reception signal, wherein the probe has a plurality of apertures, and a surface on which the plurality of transducers are arranged has a spherical surface shape.

According to the present invention, it is possible to provide technology for raising the resolution when determining property information on an object.

Further features of the present invention will become apparent from the following description of exemplary embodiments with reference to the attached drawings.

BRIEF DESCRIPTION OF THE DRAWINGS

FIGS. 4A to 4C are diagrams showing the details of a transducer;

FIGS. 7A to 7D are diagrams showing the details of the periphery of a probe;

FIGS. 9A and 9B are schematic drawings of the an object information acquiring apparatus according to a second embodiment;

DESCRIPTION OF THE EMBODIMENTS

Figure 1:
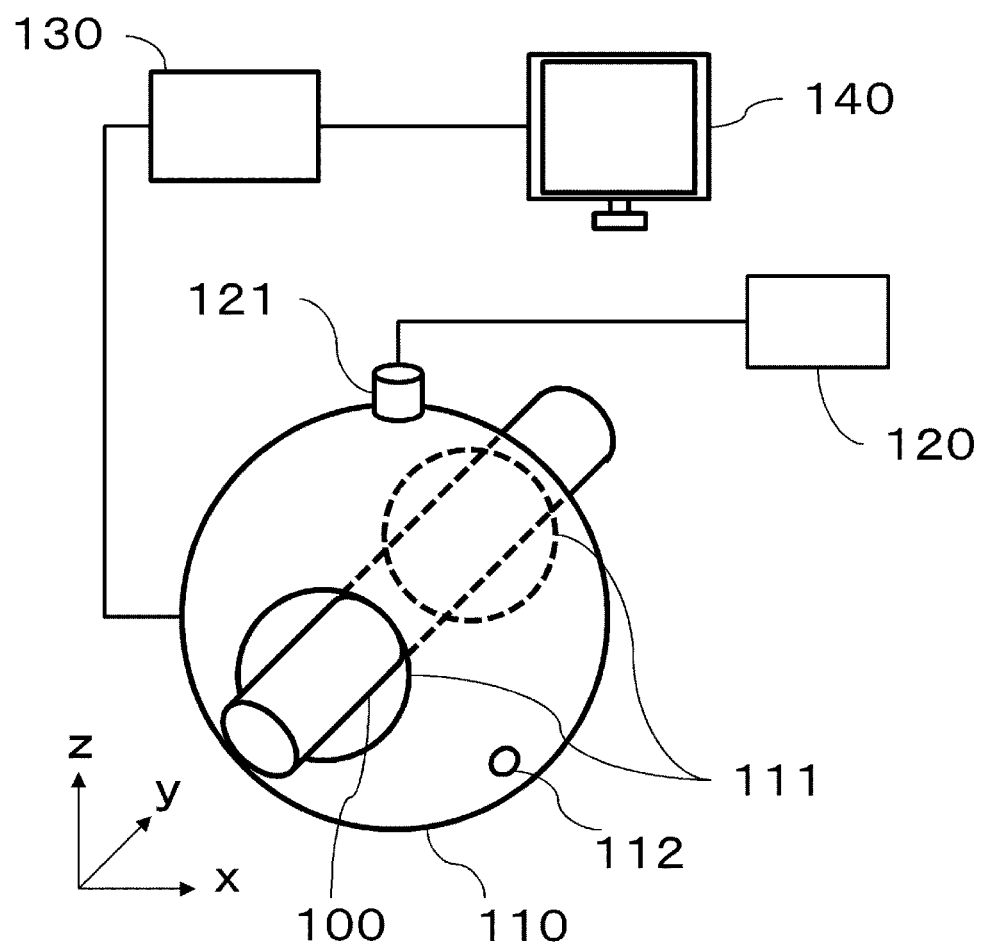
FIG. 1 is a schematic drawing of the an object information acquiring apparatus according to a first embodiment.

Below, preferred embodiments of the present invention are described with reference to the drawings. The dimensions, materials, shapes and relative arrangements, etc. of the constituent components which are indicated below should be changed, as appropriate, depending on the configuration of the apparatus to which the invention is applied, and other various conditions. Consequently, the scope of this invention is not limited to the description given below.

The present invention relates to technology for detecting an acoustic wave propagated from an object, and generating and acquiring property information on the interior of the object. Therefore, the present invention may be understood as an object information acquiring apparatus or control method for same, or an object information acquiring method or a signal processing method. The present invention may also be understood as a program which causes an information processing apparatus provided with a CPU or other hardware resources to execute these methods, or a storage medium on which this program is stored.

The object information acquiring apparatus according to the present invention includes apparatuses using photoacoustic tomography which involves shining light (electromagnetic wave) onto an object, and receiving (detecting) an acoustic wave generated and propagated at a specific position inside the object or on the surface of the object, due to a photoacoustic effect. An object information acquiring apparatus of this kind is called a photoacoustic imaging apparatus, since property information on the interior of the object is obtained in the form of image data, or the like, on the basis of photoacoustic measurement.

The property information in the photoacoustic apparatus indicates the distribution of a generation source of an acoustic wave which is generated by the irradiation of light, the initial sound pressure distribution inside the object, or a light energy absorption density distribution or absorption coefficient distribution derived from the initial sound pressure distribution, and the density distribution of the material constituting tissue. More specifically, the property information indicates the density distribution of oxygenated/reduced hemoglobin, or the blood component distribution, such as the oxygen saturation distribution, derived from the hemoglobin density distribution values, or the distribution of fat, collagen, water, or the like. Furthermore, the property information may be determined as distribution information for each position inside the object, rather than as numerical data. In other words, the object information may be distribution information, such as the absorption coefficient distribution or oxygen saturation distribution, or the like.

The acoustic wave referred to in the present invention is typically an ultrasound wave, and includes elastic waves called sound waves or acoustic waves. An acoustic wave generated by the photoacoustic effect is called a photoacoustic wave or optical ultrasound wave. An electrical signal converted from an acoustic wave by a probe is also called an acoustic signal.

<Investigation>

As stated above, "Minghua Xu and Lihong V. Wang, "Analytic explanation of spatial resolution related to bandwidth and detector aperture size in thermoacoustic or photoacoustic reconstruction", PHYSICAL REVIEW E 67, 056605 (2003)" describes a probe having a shape such as a flat surface, round cylindrical surface, spherical surface, or the like. In this respect, it is known that when photoacoustic imaging is applied to an object having a lengthwise direction using the cylindrical surface-shaped probe of "Minghua Xu and Lihong V. Wang, "Analytic explanation of spatial resolution related to bandwidth and detector aperture size in thermoacoustic or photoacoustic reconstruction", PHYSICAL REVIEW E 67, 056605 (2003)", there is a risk of decline in the resolution in the lengthwise direction of the object. An object having a lengthwise direction is, for example, an arm, leg, finger, or the like. This decline is due to the fact that the directivity axis of the transducer which is arranged on the cylindrical surface (the direction of high reception sensitivity) is aligned in a direction perpendicular to the central axis of the cylinder (in other words, the axis of the lengthwise direction of the object), and therefore the acoustic waves from directions other than the perpendicular direction cannot be received with high sensitivity.

Furthermore, since the spherical surface-shaped probe set forth in "Minghua Xu and Lihong V. Wang, "Analytic explanation of spatial resolution related to bandwidth and detector aperture size in thermoacoustic or photoacoustic reconstruction", PHYSICAL REVIEW E 67, 056605 (2003)" surrounds the object completely, then there are cases where it is difficult to arrange an object which has a lengthwise direction inside the measurable region of the probe. In particular, in cases where there are parts connected to the object having a lengthwise direction, such as the arm of a living body, it is especially difficult to arrange the object inside the probe.

Moreover, when a region of high resolution is provided within the measurable region of the probe, it is difficult to make the region of interest of the object which has a lengthwise direction overlap with the region of high resolution of the apparatus. As a result of this, there is a risk of decline in the resolution in the lengthwise direction in particular.

First Embodiment

Below, an embodiment of the present invention is described in detail with reference to the drawings. In principle, the same constituent elements are labelled with the same reference numerals in the description.

<Configuration of Object Information Acquiring Apparatus>

FIG. 1 is a schematic drawing of an object information acquiring apparatus according to the present embodiment. Below, the various constituent elements of the apparatus are described. The apparatus has a probe 110, a light source 120, an optical system 121, a controller 130 and a display unit 140. The measurement object is the object 100.

During measurement, firstly, the object 100 is irradiated with light from the light source 120 via the optical system 121. Therefore, a photoacoustic wave is generated inside the object 100 due to the photoacoustic effect. Subsequently, the probe 110 receives the photoacoustic wave that has propagated and acquires a chronological electrical signal as a reception signal. Property information on the interior of the object is obtained by analysis of the reception signal by a signal processing unit inside the controller.

Figure 2:
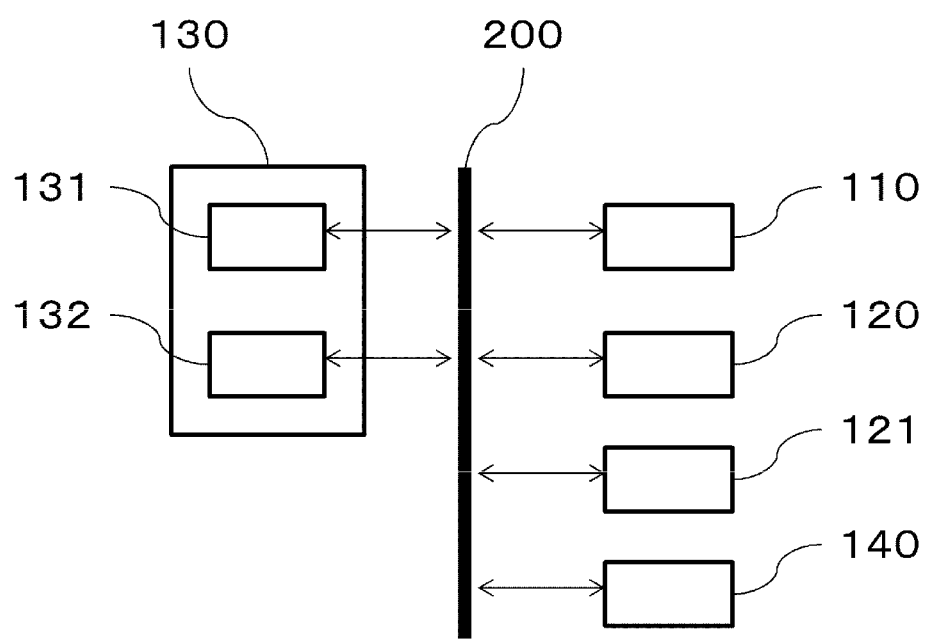
FIG. 2 is a diagram showing the configuration of a controller according to a first embodiment.

FIG. 2 is a schematic drawing showing the details of the controller 130 and the configuration peripheral to the controller 130. The controller 130 is provided with a signal processing unit 131 and a storage unit 132. The controller 130 controls the operations of the respective constituent elements of the object information acquiring apparatus via a bus 200. Furthermore, the controller 130 reads out a program defining an object information acquiring method, which is stored in the storage unit 132, to the signal processing unit 131, and causes the object information acquiring apparatus to carry out the object information acquiring method.

The storage unit 132 stores the program which defines the object information acquiring method. The storage unit 132 temporarily stores input/output data from the respective units when carrying out an imaging operation involving the entire apparatus and is capable of exchanging data between the respective units. However, each unit may also be provided with a data storage unit for carrying out various processing independently of the storage unit 132. The controller can be achieved by an information processing device provided with a processor and memory.

As shown in FIG. 1, the probe 110 according to the present embodiment is a spherical surface shape having the external appearance of a sphere, and is provided with at least two apertures 111. Therefore, it is possible to pass the object 100 which has a lengthwise direction through the spherical shape, via the two apertures 111. As a result of this, the region of interest of the object 100 can be arranged near the center of curvature of the probe 110, which is the region of high resolution, and therefore the property information on the region of interest can be acquired at high resolution.

The spherical surface shape does not necessarily mean a strictly spherical shape. Various degrees of deformation or distortion are allowable, provided that the transducer is arranged so as to surround the periphery of the object which has a lengthwise direction. For example, if the probe has an ellipsoid shape, then this is advantageous in terms of spatial efficiency. Consequently, when determining the shape of the probe, a suitable shape is chosen by taking account of the required resolution, the spatial efficiency, and other conditions.

Furthermore, in a probe, the internal surface where the transducer is arranged is desirably a spherical surface shape, but it is not essential for the outer shape of the probe to be spherical. In other words, the probe having a spherical surface shape referred to in the present invention means a probe having a transducer arrangement surface which has the shape of a spherical surface. Moreover, it is also possible to arrange various members or housings outside the probe, with the object of stabilizing the position of the object or the probe itself, and improving the usability for the patient.

(Object 100)

The object 100 does not constitute a portion of the object information acquiring apparatus according to the present invention, but is nevertheless described below. The main object of the present invention is the diagnosis of malign tumors, vascular disease, etc. in humans or animals, and the chronological observation of chemotherapy. Therefore, the object is envisaged as being a diagnosis object site in a living body, and specifically, a human or animal, etc. In particular, suitable objects are sites having a lengthwise direction, such as an arm, leg, neck region, hand, finger, etc.

Furthermore, a light absorber located inside the object has a relatively high light absorption coefficient inside the object. Examples of a light absorber are, if the measurement object is a human being, oxyhemoglobin or deoxyhemoglobin, blood vessels having large amounts of these, or malign tumors having a large number of new blood vessels. Another measurement object is plaque of the walls of the carotid artery, and the like. Moreover, the region of interest of the interior of the object may be set according to the wishes of the therapist, or the like.

(Light Source 120)

The light source 120 is desirably a pulse light source which is capable of generating light pulses of the order of several nanoseconds to several microseconds. In order to generate a photoacoustic wave efficiently, it is desirable to use light having a pulse width of approximately 10 nanoseconds. The wavelength of the pulse light is desirably a wavelength of light which propagates to the inside of the object. More specifically, if the object is a living body, then a wavelength of no less than 500 nm and no more than 1200 nm is suitable. If the living body tissue relatively near the surface of the body is to be measured, then it is possible to use light in a broader wavelength range (for example, 400 nm to 1600 nm), because the amount of decay is small.

Suitable lights sources are laser light sources, such as a solid laser, gas laser, dye layer, semiconductor laser, and the like. For example, it is possible to use an alexandrite laser, Yttrium-Aluminum-Garnet laser, Titan-Sapphire laser, and the like. Furthermore, it is also possible to use a light-emitting diode or a flash lamp, etc.

(Optical System 121)

The light emitted from the light source 120 is shaped into a desired light distribution shape by the optical system 121 which includes various optical components, and is directed onto the object 100 at a desired intensity. The optical components are, for instance, mirrors which reflect light, lenses which concentrate, expand, or change the shape of the light, prisms which disperse, refract or reflect the light, optical waveguides, such as optical fibers, diffusion plates which diffuse the light, and so on. Any kind of optical component can be used, provided that the object can be irradiated with light of the desired shape and intensity.

The intensity of the light radiated onto the object 100 from the optical system 121 may be set in advance and stored in the storage unit 132. The controller 130 drives the light source 120 so as to emit irradiation light at the set intensity. Alternatively, a light sensor may be provided in the light source 120 or the optical system 121, and the intensity of the irradiation light may be determined by measuring a portion of the light that is actually emitted, and stored in the storage unit 132. The light intensity can be utilized as a correctional amount to improve the quantitative properties of the portion of the property information that is dependent on the light intensity. If the light source 120 itself is capable of radiating light of the desired shape and intensity, then the optical system 121 is not necessary. The optical system 121, or the light source 120, or a combination of these corresponds to the irradiator of the present invention.

(Probe 110)

The probe 110 is provided with a transducer 112 which outputs an analog electrical signal upon receiving an acoustic wave, and a housing which surrounds the transducer. The transducer 112 is arranged in such a manner that the direction of high sensitivity (directivity axis) is directed towards the inside of the spherical shape. Any transducer 112 may be used, such as transducers using change in a piezoelectric effect, light resonance, electrostatic capacitance, or the like. Since the frequency component of the photoacoustic wave is typically in the range of 100 kHz to 100 MHz, then it is desirable for the transducer 112 to be able to detect acoustic waves of these frequencies.

In order to obtain an image of high resolution, it is desirable for the probe to have a plurality of transducers, which are arranged at a plurality of measurement positions. Consequently, a photoacoustic wave generated by one light irradiation operation can be acquired at a plurality of positions, and therefore the amount of information used for image creation is increased and the image quality is improved. In this case, a high-resolution region where the directivity axes of the transducers come together is formed inside the spherical body. A single transducer may be moved to a plurality of measurement positions. The analog electrical signal output by the transducer 112 is subjected to an amplification process and a digital conversion process, according to requirements, and is then reconstructed as property information.

Figure 3A:
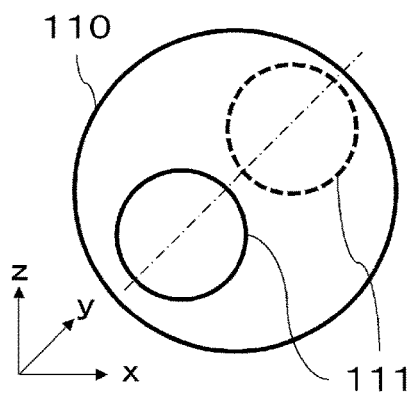
FIGS. 3A to 3D are diagrams showing the details of a probe.
Figure 3B:
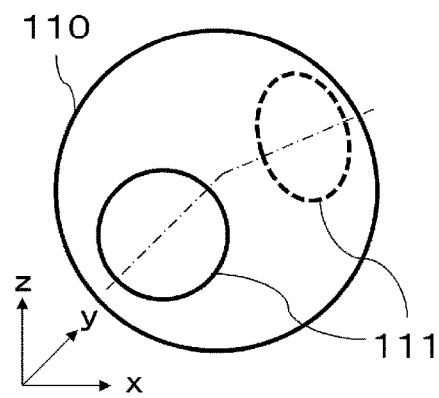
Figure 3C:
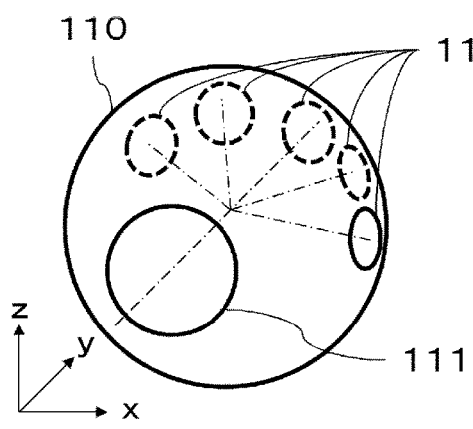

The probe 110 in the present embodiment has a spherical surface shape, and has a plurality of apertures 111. A probe 110 in which two apertures 111 are arranged on opposing surfaces as in FIG. 3A is suitable for measurement of an arm, leg or cervical part, etc. A probe 110 having an aperture arrangement as shown in FIG. 3B is suitable for measurement of a joint, such as a knee, elbow, ankle, wrist, hip joint, shoulder, and the like. A probe 110 having the aperture arrangement such as that in FIG. 3C is suitable for measurement of the palm of a hand. The shape of the probe 110 is not limited to these shapes, provided that at least two apertures 111 are provided.

Figure 3D:
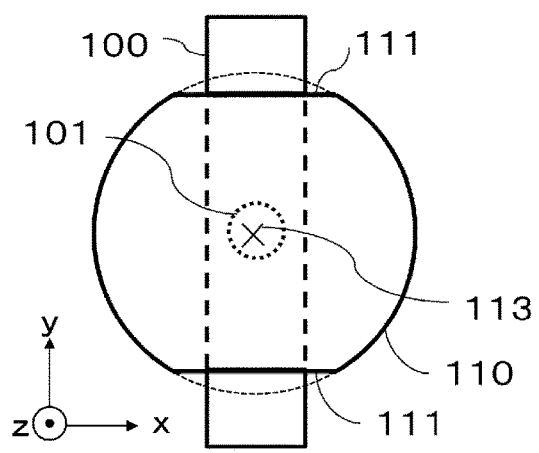

By using a probe 110 having at least two apertures as described above, as shown in FIG. 3D the region of interest 101 of the object 100 can be arranged near the center of curvature 113 of the probe 110, which is the region of high resolution. The apertures 111 correspond to the apertures of the present invention.

FIGS. 4A to 4B are detailed diagrams of a probe 110 having a plurality of transducers 112. In FIG. 4A, a plurality of transducers 112 are arranged in a spiral configuration on the spherical surface inside the probe 110. In FIG. 4B, the plurality of transducers 112 are disposed in a radiating fashion. In FIG. 4C, tile-shaped transducers 112 are laid together on the surface. In each of these cases, the photoacoustic wave generated by the object 100 can be received from a variety of angular directions. The arrangement of the transducers is not limited to a spiral shape, radiating shape or tile shape. For instance, a lattice-shaped arrangement and random arrangement is also possible.

The space between the transducer arrangement surface of the probe 110 and the object 100 is filled with a medium that is capable of propagating photoacoustic waves. This medium is desirably one which produces as small a change as possible in the acoustic properties at the interface with the object 100 and the transducers 112, and which has as high a transmissivity as possible with respect to photoacoustic waves. Furthermore, desirably, the medium has a high transmissivity with respect to light, so that the light from the optical system 121 is radiated efficiently onto the object 100.

Figures 5A, 5B:
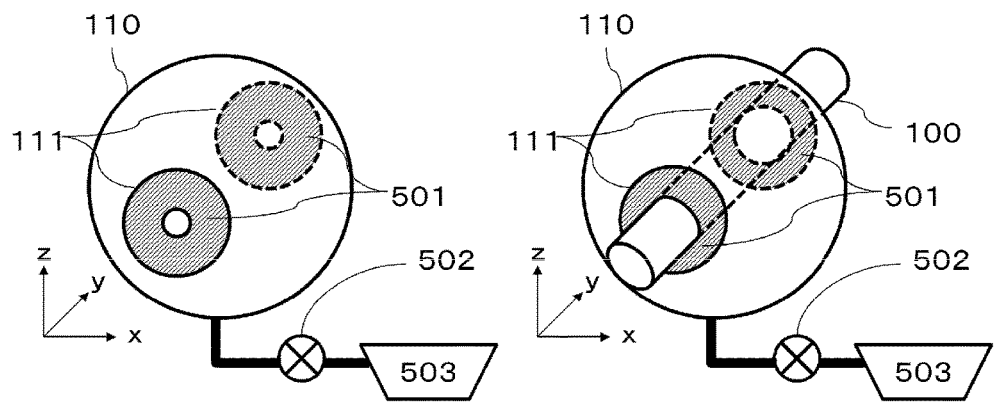
FIGS. 5A and 5B are diagrams showing the details of a seal.

As shown in FIGS. 5A and 5B, when not performing measurement, the medium may be stored in a tank 503. In this case, the medium is injected into the space inside the probe 110 by a pump 502 when measurement is to be performed, and the medium is returned to the tank 503 by the pump 502 when measurement has been completed. The pump 502 is connected to the bus 200 in FIG. 2, and injects and discharges the medium in accordance with controls from the controller 130. Alternatively, an operator may operate the pump 502 directly. The medium corresponds to the matching medium of the present invention. The pump 502 corresponds to the medium supplier.

The medium is desirably a material such as a liquid or a gel, etc. which can deform in accordance with the shape of the object 100. For instance, it is possible to use water, castor oil, ultrasound matching gel, or the like. In this case, it is desirable to provide seals for suppressing leaking of the medium from the apertures 111 of the probe 110.

FIG. 5 shows sealing sections 501 as one type of seal. The sealing sections 501 are made from a material that is expandable and contractible, such as rubber, and have a hole formed therein in order to introduce the object 100. When the object 100 is introduced through the holes, then as shown in FIG. 5B, the sealing sections 501 make tight contact with the object 100, and prevent leaking of the medium. When the holes for introducing the object 100 are small enough and the amount of leakage of medium is small, then the interior of the probe 110 may be filled with the medium at all times. In this case, the pump 502 and the tank 503 can be omitted.

FIGS. 6A to 6D show bags 601 as another type of seal. The bags 601 provided inside the probe are made from a material that is expandable and contractible, such as rubber. When the pump 502 injects the medium inside the bag 601 which is a compressed state as in FIG. 6A, the bag 601 swells as in FIG. 6B. By causing the bag to swell until reaching a state of making satisfactory tight contact with the whole area of the object 100 and the probe 110 as in FIG. 6B, the interior of the probe 110 is filled with the medium. Furthermore, since the medium is sealed inside the bag, then the medium does not leak out from the apertures. Furthermore, by forming a bag shape so as to hold the object 100 when swollen, it is possible to achieve a beneficial effect in that the object 100 is held and fixed securely.

Figure 6A:
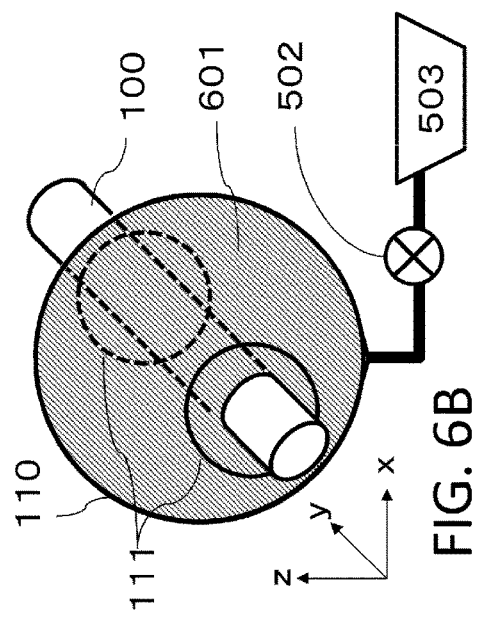
FIGS. 6A to 6D are diagrams showing the details of a bag.
Figure 6B:
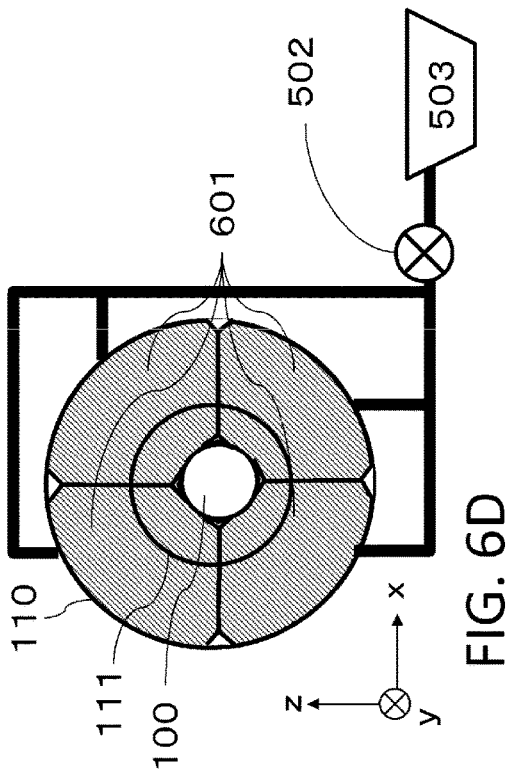
Figure 6C:
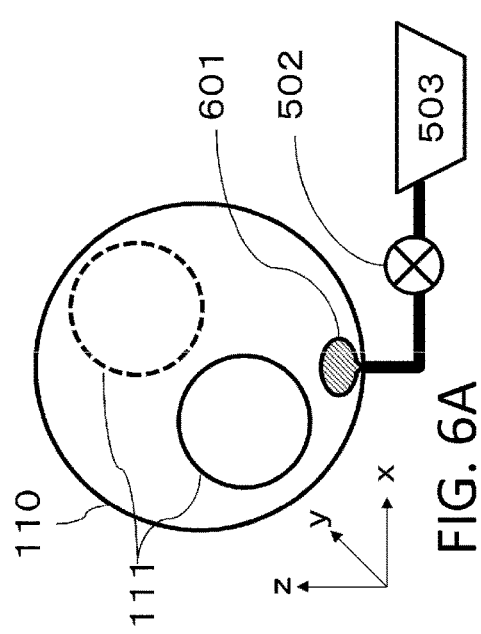
Figure 6D:
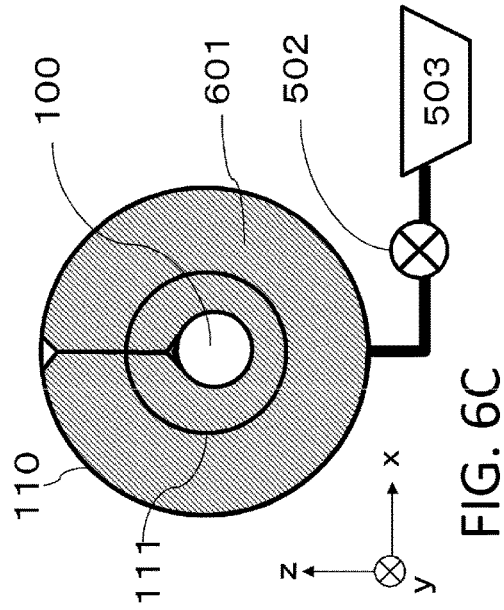

FIG. 6C shows a case where there is one bag 601, and in this case, the bag 601 swells so as to enclose the object 100. Furthermore, it is also possible to provide a plurality of bags 601 as shown in FIG. 6D. In this case, the medium is supplied from the pump 502 to the space inside the bags. Consequently, the bags 601 efficiently enclose the object 100.

When the bags 601 have swollen, there is a possibility of small gaps occurring between, for example, the object 100 or the probe 110, and, the bags 601. Consequently, a small amount of medium is introduced previously inside the probe 110, so as to fill in the gaps with the medium when the bags 601 swell up. Furthermore, it is also possible to use bags 601 which are in a swollen state at all times. In this case, bags 601 which can deform in accordance with the shape of the object 100 are used. According to this configuration, the pump 502 and the tank 503 can be omitted.

For the bags 601, it is desirable to use a material by which the acoustic properties are matched at the interface with the object 100 or the transducers 112, and a material having as high a transmissivity as possible with respect to photoacoustic waves. Furthermore, a material having high transmissivity with respect to the light from the optical system 121 is desirable. For purposes of hygiene, the bags 601 are desirably removable from the probe 110. Therefore, when measuring a plurality of objects 100, every part of the bags can be sterilized for each object. Furthermore, the bags 601 may also be configured to be disposable. Therefore, it is possible to achieve efficient measurement by replacing the bags 601 for each object.

A holding section 701 for holding the object 100 may be provided on the outside of the aperture 111, as in FIGS. 7A to 7D. The region of interest 101 can be arranged securely near the center of curvature 113 of the probe 110, by the holding section 701. Moreover, the arrangement accuracy of the region of interest is improved by providing a mechanism for adjusting the positional relationship of the holding section 701 and the probe 110. One example of a mechanism of this kind is the holder movement section 702 shown in FIG. 7A. The holder movement section 702 can move the holding section 701 in parallel with the probe 110 and rotate the holding section 701 with respect to same.

Furthermore, the probe moving section 703 shown in FIG. 7B may also be provided. The probe moving section 703 moves the probe 110 in parallel with the holding section 701 and rotates the probe 110 with respect to same. In order to achieve highly accurate positional adjustment, the greater the number of parallel movement and rotational axes, the better, but the number of axes should be adjusted to achieve a trade-off with the complexity and cost of the apparatus. The probe moving section 703 corresponds to the mover of the present invention.

The probe 110 can be split as shown in FIG. 7C. If the probe 110 can be split, then the region of interest 101 can be viewed, and therefore the positioning of the region of interest 101 at the center of curvature 113 is facilitated. When the probe 110 is large or heavy, then a hinge 704 may be provided.

As shown in FIG. 7D, a position measurement unit 705, such as a camera, may be provided in the probe 110. By using the position of the object 100 or the region of interest 101 acquired by the position measurement unit 705, it is possible to arrange the region of interest 101 with good accuracy near the center of curvature 113. In order to ascertain the spatial positional relationship between the region of interest 101 and the center of curvature 113, three or more cameras may be arranged so that the optical axes thereof are mutually orthogonal, as far as possible, while also facing the center of curvature 113. Apart from a camera, it is also possible to use a laser displacement meter or laser shape measurement device, or the like, as the position measurement unit 705.

Moreover, it is also possible to provide a target projection unit facing the center of curvature, whereby the positional relationship can be easily ascertained by projecting markings onto the object 100. A laser pointer or laser grid can be used as the target projection unit.

(Signal Processing Unit 130)

The controller 130 is provided with a signal processing unit 131 and a storage unit 132, as shown in FIG. 2. The controller 130 excluding the storage unit 132 is typically configured by elements, such as a CPU, GPU, A/D converter, and circuits such as an FPGA, ASIC, etc. Furthermore, it is also possible to include a signal amplifier. Because the electrical signal converted from the acoustic wave by the transducers 112 is an analogue signal, then the signal is usually converted to a digital signal and subjected to an amplification process. The signal processing unit 131 may also be configured by a plurality of elements or circuits, rather than being configured by a single element or circuit. Furthermore, the processes for acquiring object information may be carried out by any of the elements or circuits. The devices which carry out the respective processes are generally referred to as the signal processing unit according to the present embodiment.

The storage unit 132 is typically configured by a storage medium, such as a ROM, RAM and hard disk, etc. The storage unit 132 may also be configured by a plurality of storage media, rather than being configured by a single storage medium. Furthermore, the signal processing unit 131 is desirably capable of carrying out pipeline processing of a plurality of signals simultaneously, in order to shorten the processing time. It is possible to save the property information acquisition process in the storage unit 132 as a program which is executed in the signal processing unit 131. However, the storage unit 132 in which the program is stored is a non-temporary recording medium.

The signal processing unit 131 and the plurality of transducers 112 may be accommodated in a common housing. A portion of the signal processing may be carried out by a signal processing unit accommodated in the housing, and the remainder of the signal processing may be carried out by a signal processing unit provided outside the housing. In this case, the signal processing unit(s) provided inside and outside the housing is referred to generally as the signal processing unit according to the present embodiment.

(Display Unit 140)

The display unit 140 is a device which displays property information that is output from the signal processing unit 131. The display unit 140 may use a liquid crystal display, a plasma display, an organic EL display, an FED, or the like. The display unit 140 is not essential and may also be provided separately from the object information acquiring apparatus.

<Object Information Acquiring Method>

Figure 8:
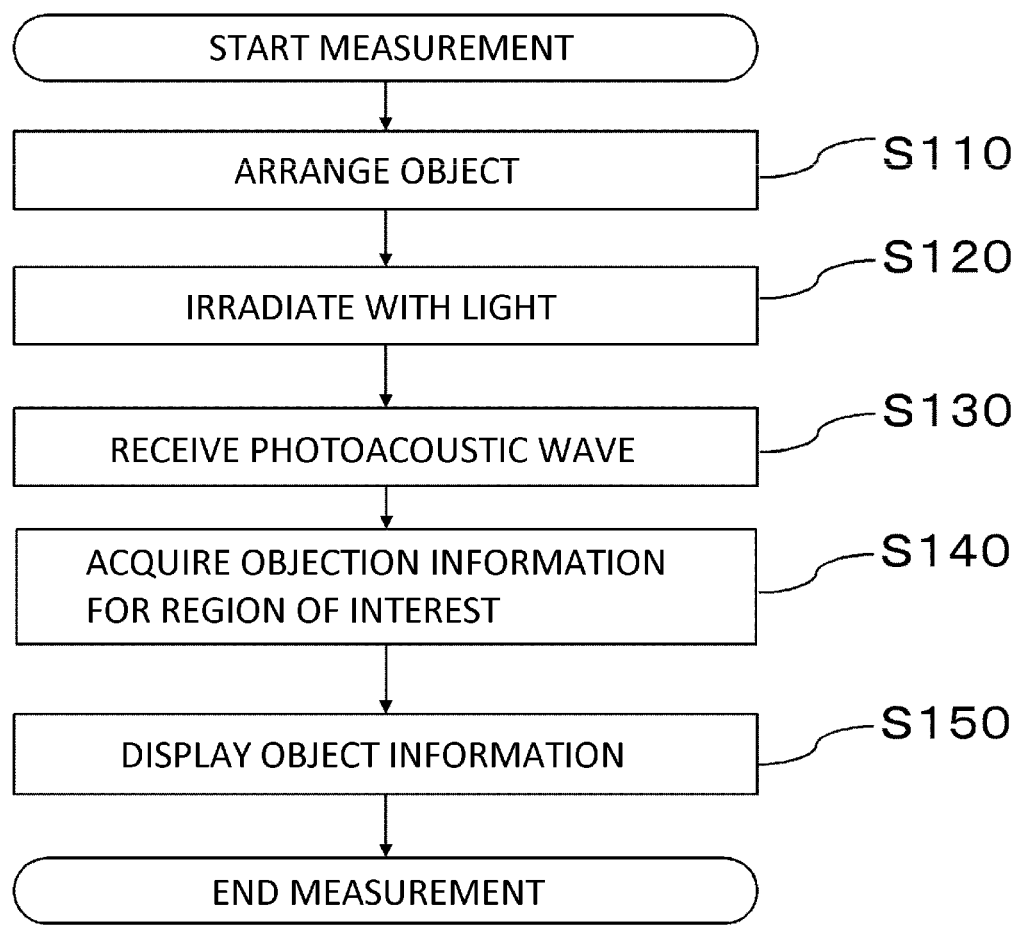
FIG. 8 is a flow chart of an object information acquiring method according to a first embodiment.

Next, the respective steps of the object information acquiring method relating to the present embodiment are described with reference to FIG. 8. Each step is carried out by means of the controller 130 controlling the operation of the respective constituent parts of the object information acquiring apparatus.

(S110: Step of Arranging Object)

In this step, the region of interest 101 of the object 100 is arranged near to the center of curvature 113 of the probe 110, which is the region of high resolution. The object 100 is introduced into the probe 110 so as to pass through the two apertures 111, and the positional relationship between the probe 110 and the object 100 is adjusted. After completing the arrangement of the object 100, the pump 502 injects the medium.

(S120: Step of Generating a Photoacoustic Wave by Irradiating the Object with Light)

In this step, the object 100 is irradiated with light generated by the light source 120 via the optical system 121. In so doing, the light is absorbed by the inside of the object 100, and a photoacoustic wave is generated by the photoacoustic effect.

(S130: Step of Receiving Photoacoustic Wave and Acquiring and Saving Reception Signal)

In this step, the photoacoustic wave is received (detected) by the probe 110, and a reception signal is output. The output reception signal is stored in a storage unit 132.

(S140: Step of Acquiring Object Information in Region of Interest)

In this step, property information is acquired for the region of interest 101 by using the reception signal acquired in step S130. When the photoacoustic wave generation source distribution, in other words, the initial sound pressure distribution, is acquired as the property information, then it is possible to use a reverse projection method of the temporal region or frequency region, which is a generic image reconstruction method. Furthermore, it is also possible to use a timer reversal method which solves a wave motion equation by reversing the time, or a model base method which solves the problem of optimization by modelling a series of measurements.

When information relating to the absorption coefficient distribution is acquired as property information, the light intensity distribution of the region of interest 101 at the moment of generation of the photoacoustic wave is acquired, and the abovementioned initial sound pressure distribution is divided by the light intensity distribution. The light intensity distribution is acquired by solving a transport equation or light distribution equation by a Monte Carlo method, finite element method, differential method, and the like. In this case, the light intensity distribution can be calculated more accurately by using the values of the light intensity of irradiated light saved in the storage unit 132.

(S150: Step of Displaying Object Information)

In this step, the property information on the region of interest acquired in S140 is displayed on the display unit 140. The object information on the region of interest 101 displayed on the display unit 140 has a high resolution, and therefore is suitable for diagnosis and the like by the operator, such as a doctor. This step is not essential to the present invention, and it is also possible to acquire highly accurate property information and store same in a storage apparatus for separate use.

According to the object information acquiring method according to the present embodiment described above, a reception signal is generated from a photoacoustic wave generated in a region of high resolution, and the property information on the region of interest 101 can be acquired at high resolution. In particular, even if the object has a lengthwise direction, then the photoacoustic wave can be detected from a variety of directions, and the resolution in the lengthwise direction does not decline.

Second Embodiment

In the present embodiment, the accuracy of arrangement of the region of interest of the object, in the region of high resolution, is improved compared to the first embodiment. In principle, the same constituent elements as the first embodiment are labelled with the same reference numerals and description thereof is omitted.

<Configuration of Object Information Acquiring Apparatus>

FIGS. 9A and 9B are schematic drawings of an object information acquiring apparatus according to the present embodiment.

(Bag 901)

Figure 10:
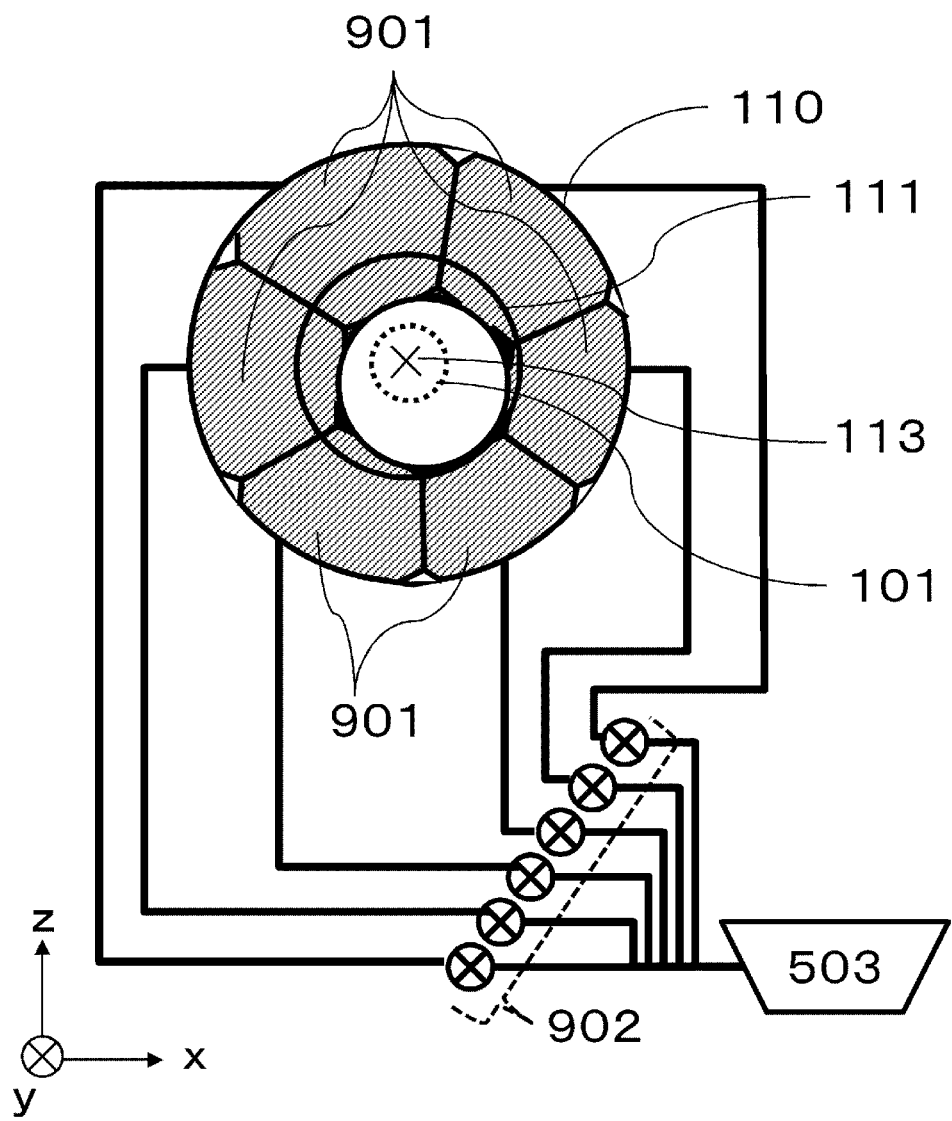
FIG. 10 is a diagram showing the details of a plurality of bags.

The apparatus according to the present embodiment has a plurality of bags 901 which are similar to the bags 601 described in the first embodiment. Moreover, the amount of medium injected into the bags can be adjusted individually. Consequently, as shown in FIG. 10, there is a variation in the relative volume ratios of the bags 901 when swollen. In the present embodiment, a case where there are six bags 901 has been described, but there is no limit on the number of bags provided that there are at least two bags.

(Pumps 902)

The pumps 902 have a similar function to the pump 502 described in the first embodiment, and in addition to this, are capable of individually adjusting the amounts of medium injected into the plurality of bags 901. It is possible for a single pump 902 to inject the medium into a plurality of bags 901, or for a number of pumps 902 corresponding to the number of bags to be prepared. The pumps 902 are connected to the bus 200 in FIG. 2, and introduce and discharge the medium to the individual bags in accordance with controls from the controller 130. Alternatively, an operator may directly operate the pumps 902 individually. The pump 902 corresponds to a medium supplier.

<Object Information Acquiring Method>

Figure 11:
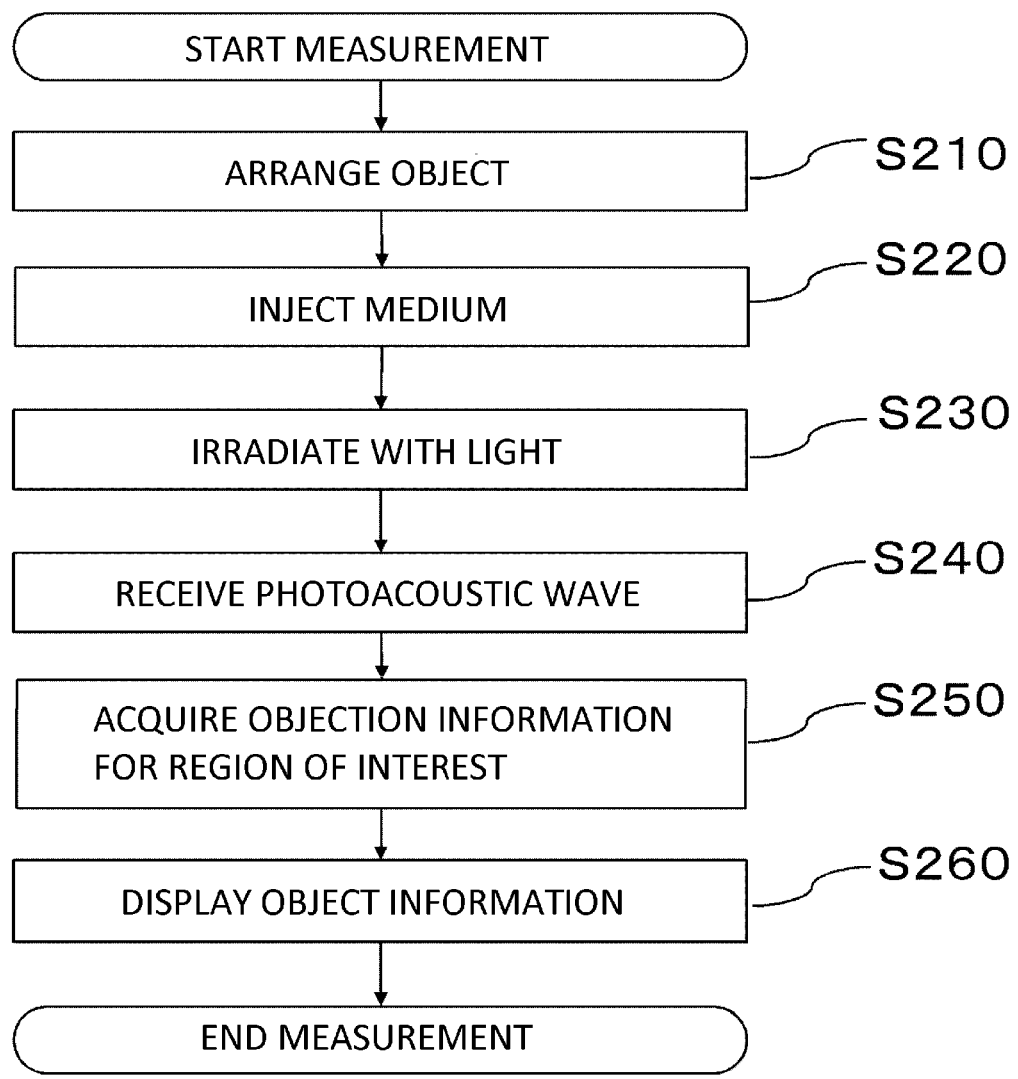
FIG. 11 is a flow chart of an object information acquiring method according to a second embodiment.

Next, the respective steps of the object information acquiring method relating to the present embodiment are described with reference to FIG. 11. Each step is carried out by means of the controller 130 controlling the operation of the respective constituent parts of the object information acquiring apparatus. Steps S210, S230, S240, S250, S260 in FIG. 11 are respectively the same as S110, S120, S130, S140 and S150 in FIG. 8, and description thereof is omitted here.

(S220: Step of Injecting Medium)

In this step, the medium is injected into the bags 901 by the pumps 902. The amount of medium injected into the individual bags 901 is determined on the basis of the positional relationship of the object 100 with respect to the center of curvature 113 or the shape of the object 100. For example, the operator visually ascertains the positional relationship and shape in step S210, and makes the amount of injected medium smaller, in the bags 901 towards the side where the distance from the surface of the object 100 to the center of curvature 113 is long (deep). In FIG. 10, the distance from the bottom right surface of the object 100 to the center of curvature 113 is long. Therefore, the amount of medium present in the bags located on the bottom right of the probe 110 is made smaller. Consequently, it is possible to prevent the arranged object 100 from being pushed and moved by the bags, and moved away from a suitable position.

The amounts of medium injected into the individual bags 901 can also be adjusted, without involving the operator. The position measurement unit 705 described in the first embodiment (a laser shape measurement device, etc.) is provided in the probe 110 according to the present embodiment, and the shape or position of the object 100 is measured prior to the injection of the medium. The adjustment which was performed by an operator in the description given above can be automated by the controller 130 individually controlling the pumps 902 so as to adjust the amount of medium injected into the individual bags 901, on the basis of this shape or position.

According to the object information acquiring method of the present embodiment, since the region of interest 101 can be arranged with higher accuracy in the region of high resolution, then it is possible to acquire property information for the region of interest 101 with even higher resolution.

Third Embodiment

In the present embodiment, it is possible to acquire the property information on the region of interest of the object at high resolution and higher contrast, compared to the first embodiment. In principle, the same constituent elements as the first and second embodiments are labelled with the same reference numerals in the description.

<Configuration of Object Information Acquiring Apparatus>

Figure 12:
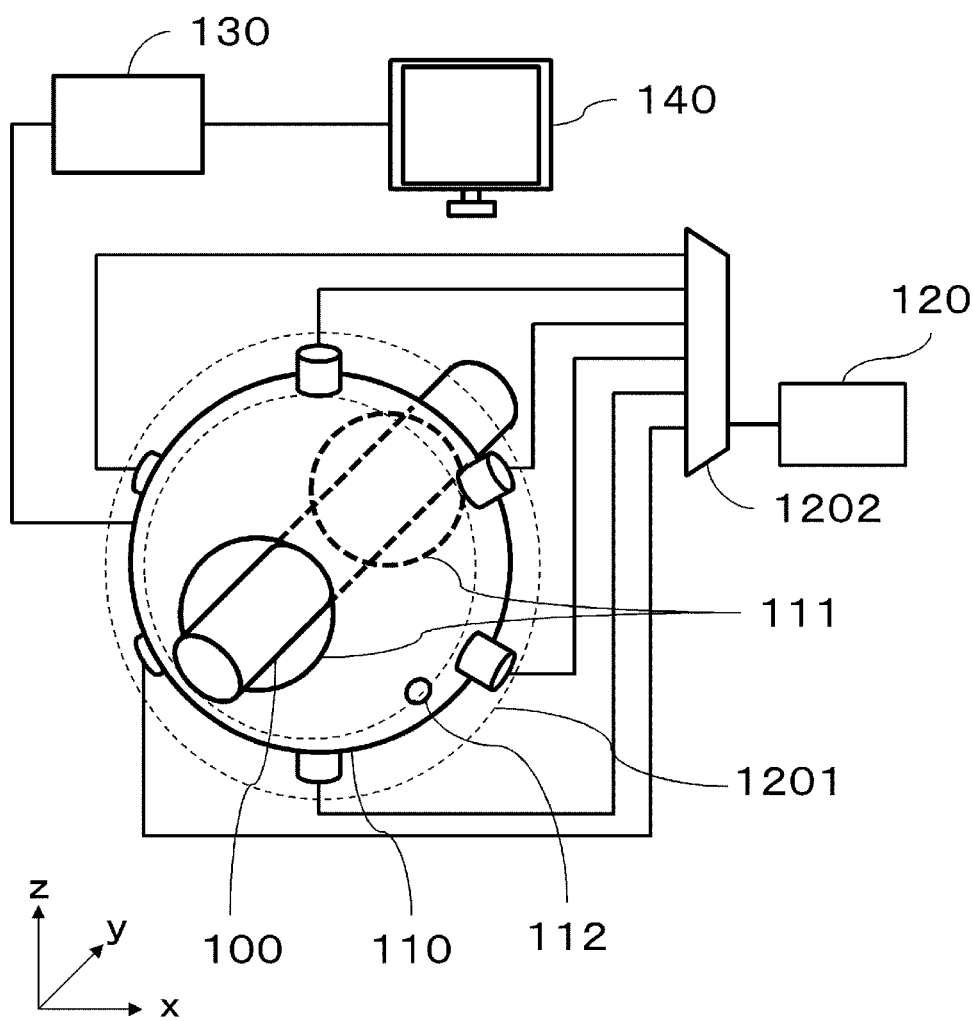
FIG. 12 is a schematic drawing of the an object information acquiring apparatus according to a third embodiment.

FIG. 12 is a schematic drawing of an object information acquiring apparatus according to the present embodiment.

(Optical System 1201)

In FIG. 12, the plurality of round cylinders in the region enclosed by the dotted line labelled with reference numeral 1201 are the optical system 1201 of the present embodiment. The optical system 1201 has similar materials and functions as the optical system 121 described in the first embodiment. In the present embodiment, a plurality of optical systems of this kind are present and the optical system that is to radiate light can be selected from these. In the present embodiment, a case is shown in which there are six optical systems, but the number thereof is not limited to this.

Figure 13:
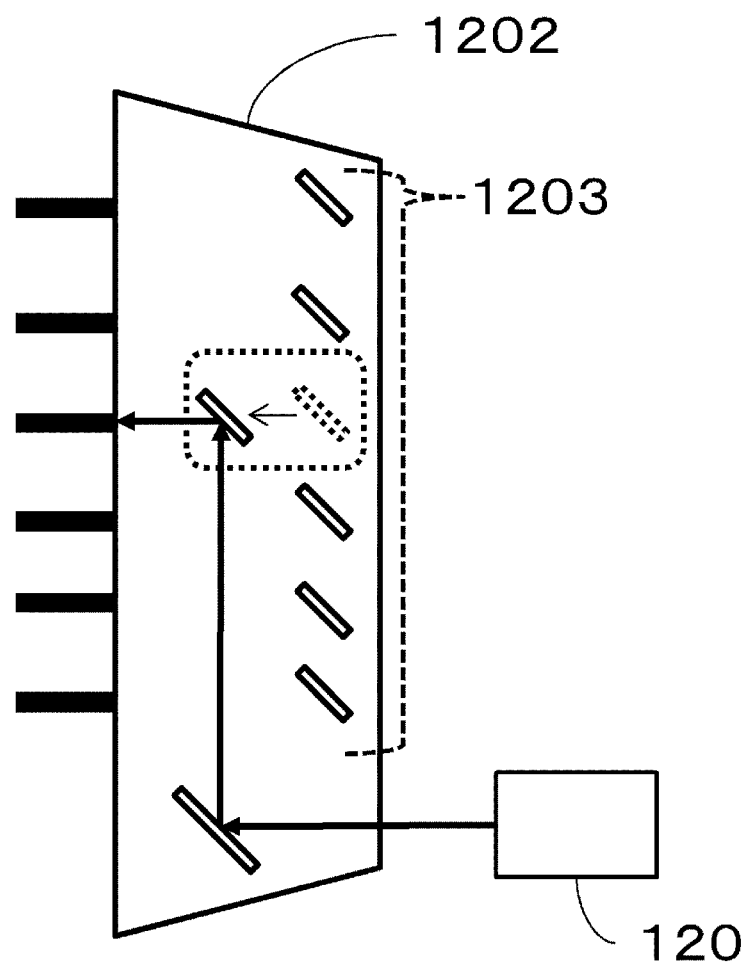
FIG. 13 is a diagram showing the details of a switching device.

The optical system 1201 which is to radiate light is selected by a switching device 1202. FIG. 13 shows an example of the switching device 1202. The switching device 1202 has a plurality of movable mirrors 1203, and these movable mirrors correspond respectively to each of the optical systems 1201. As indicated by the dotted square shape in FIG. 13, light is radiated from the corresponding optical system 1201 by moving one of the movable mirrors 1203 into the light path from the light source 120. The switching device 1202 is connected to the bus 200 and operates in accordance with the control by the controller 130. There are no restrictions on the structure of the switching device, and it is also possible to use a shutter mechanism or transmissivity changing function, for example.

The optical systems 1201 are desirably arranged in such a manner that the respective optical axes thereof are perpendicular to the long axis direction of the object 100, and so as to surround the object 100. Consequently, a desired position on the object 100 can be irradiated with light, with a high irradiation density. Due to this configuration, since the required amount of light is delivered to the region of interest, the SN ratio of the photoacoustic wave is raised. When using a laser light source, in particular, the intensity of the irradiation light is controlled so as to satisfy safety standards, such as the maximum permissible exposure (MPE).

<Object Information Acquiring Method>

Next, the respective steps of the object information acquiring method relating to the present embodiment will be described. Each step is carried out by means of the controller 130 controlling the operation of the respective constituent parts of the object information acquiring apparatus. The processing flow is similar to FIG. 8, and the details of the light irradiation step in S120 are different.

Figure 14:
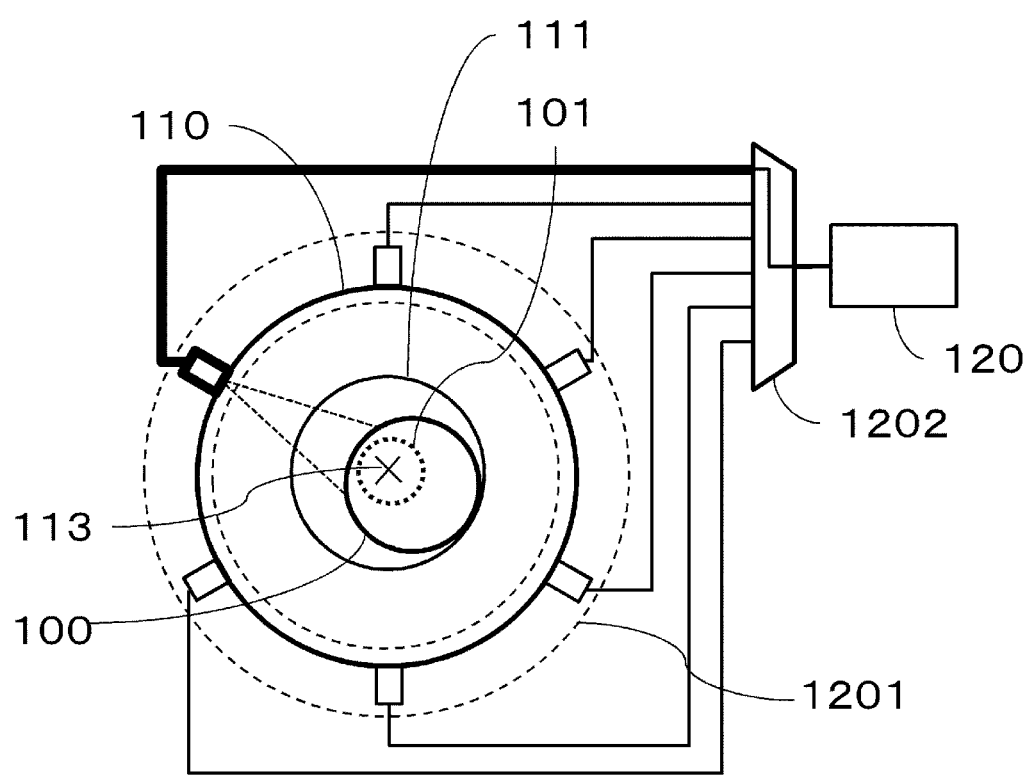
FIG. 14 is a diagram showing the details of light irradiation according to a third embodiment.

In S120 according to the present embodiment, firstly, the optical system which is to radiate light from a plurality of optical systems 1201 is selected. The object 100 is irradiated with light from the light source 120 via the selected optical system 1201. The optical system is selected on the basis of the positional relationship of the object 100 with respect to the center of curvature 113 or the shape of the object 100. The operator, for example, visually ascertains the positional relationship or shape, and selects the optical system 1201 situated on the side where the distance from the surface of the object 100 to the center of curvature 113 is short (shallow). In FIG. 14, since the distance from the upper left surface of the object 100 to the center of curvature 113 is short, then the optical system 1201 indicated by the thick lines, which is situated at the upper left of the probe 110, is selected.

The selection of the optical system 1201 can be performed without involving the operator. The position measurement unit 705 described in the first embodiment (a laser shape measurement device, etc.) is provided in the probe 110 according to the present embodiment, and the shape or position of the object 100 is measured prior to the injection of the medium. The amount of light adjustment can be automated by the controller 130 selecting one from among the plurality of optical systems 1201, on the basis of this shape or position. Furthermore, the selected optical system is not limited to being one system. Moreover, it is also possible to make the amount of liquid adjustable for each optical system.

The object 100, such as a living body, generally scatters and absorbs the light strongly, and therefore it is known that the intensity of the irradiated light decays exponentially in the depth direction of the object. Therefore, the light intensity of shallow region of the object is stronger than that of deep region. In the present embodiment, the surface of the object 100 which is at a shallow distance from the center of curvature 113 is irradiated selectively with light, and therefore, the light efficiently reaches the region of interest which coincides with the vicinity of the center of curvature 113. Consequently, the amplitude of the photoacoustic wave becomes greater in proportion with the intensity of arriving light, and the SN ratio of the reception signal can be improved. By using a reception signal having a high SN ratio generated in the region of high resolution, it is possible to acquire property information for the region of interest, at high resolution and high contrast.

Fourth Embodiment

The present embodiment describes an object information acquiring apparatus which is capable of acquiring property information for a broader region of interest, at high resolution, by scanning the probe with respect to the object. In principle, the same constituent elements as the first or second embodiments are labelled with the same reference numerals, and description thereof is omitted here.

<Configuration of Object Information Acquiring Apparatus>

Figure 15:
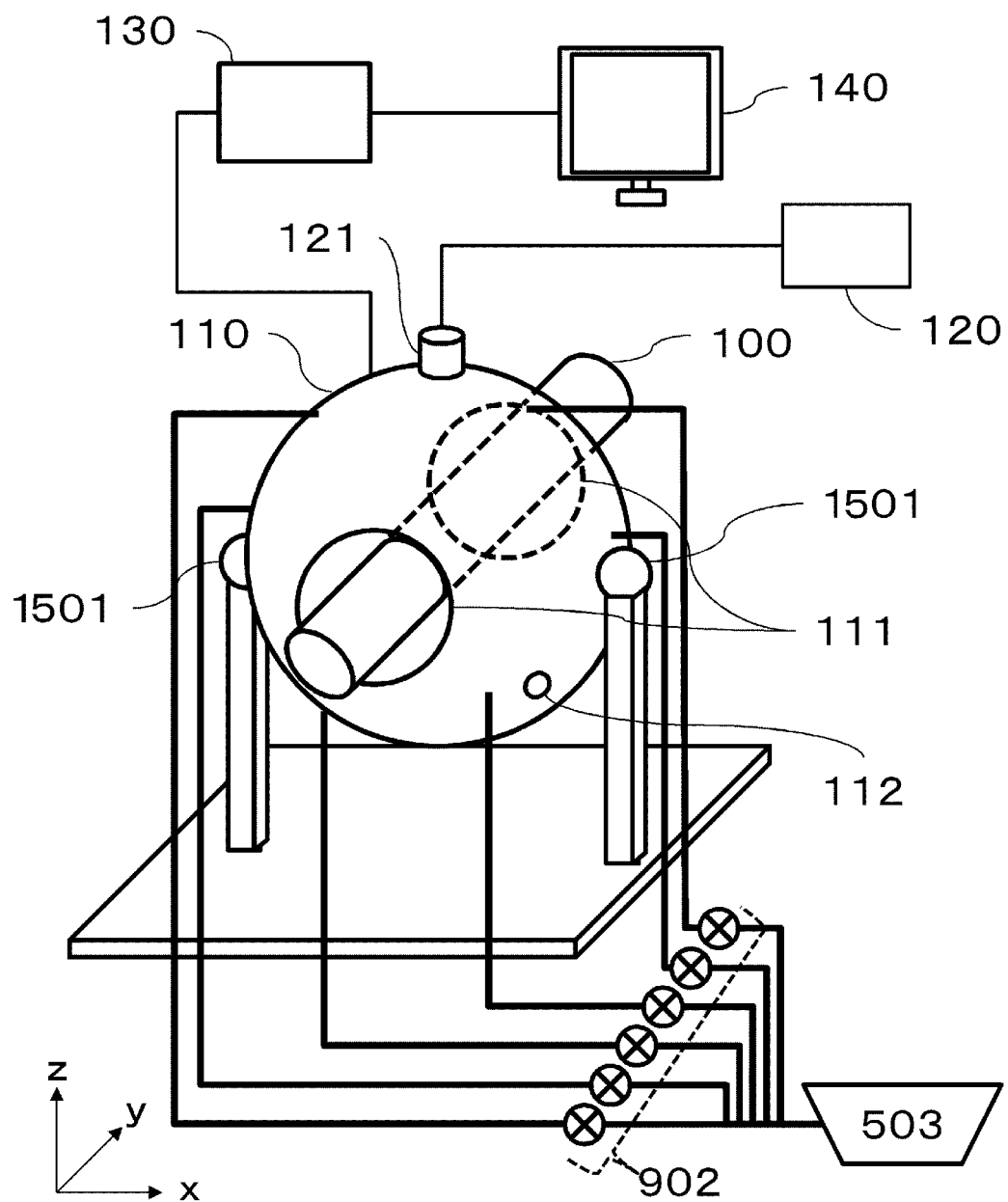
FIG. 15 is a schematic drawing of the an object information acquiring apparatus according to a fourth embodiment.

FIG. 15 is a schematic drawing of the object information acquiring apparatus according to the present embodiment, in which the probe moving section shown in FIG. 7B is installed on the object information acquiring apparatus according to the second embodiment shown in FIGS. 9A and 9B.

(Probe Moving Section 1501)

The probe moving section 1501 according to the present embodiment has the same functions as the probe moving section 703 described in the first embodiment. Moreover, the probe moving section 1501 has a scanning function for moving the probe 110 relative to the object 100 in accordance with controls by the controller 130.

Figure 16A:
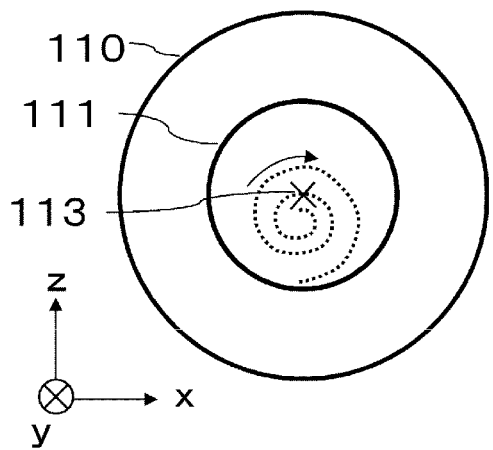
FIGS. 16A to 16C are diagrams showing a scanning trajectory.
Figure 16B:
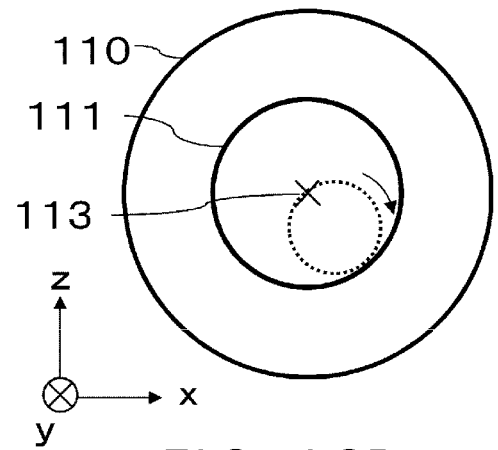
Figure 16C:
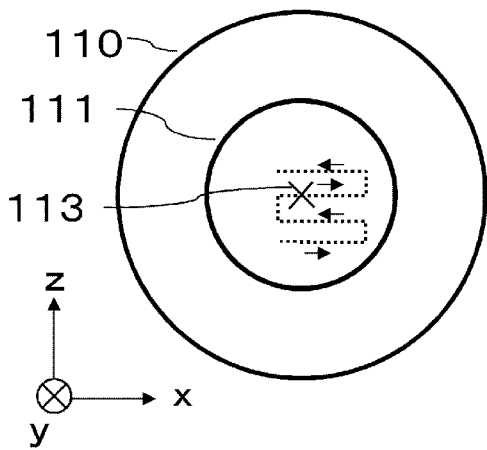

FIGS. 16A to 16C show examples of a scanning trajectory. FIG. 16A shows scanning along a spiral trajectory, FIG. 16B shows a circular operation trajectory and FIG. 16C shows scanning along a linear trajectory. These trajectories can be selected, as appropriate, in accordance with the shape of the region of interest, and the like. Furthermore, FIGS. 16A to 16C are examples, and other scanning trajectories may be used. Although not shown in the drawings, a plurality of the bags 901 shown in FIG. 9B are disposed inside the probe 110, and the medium can be injected into and discharged from each of the bags by a pump 902.

<Object Information Acquiring Method>

Figure 17:
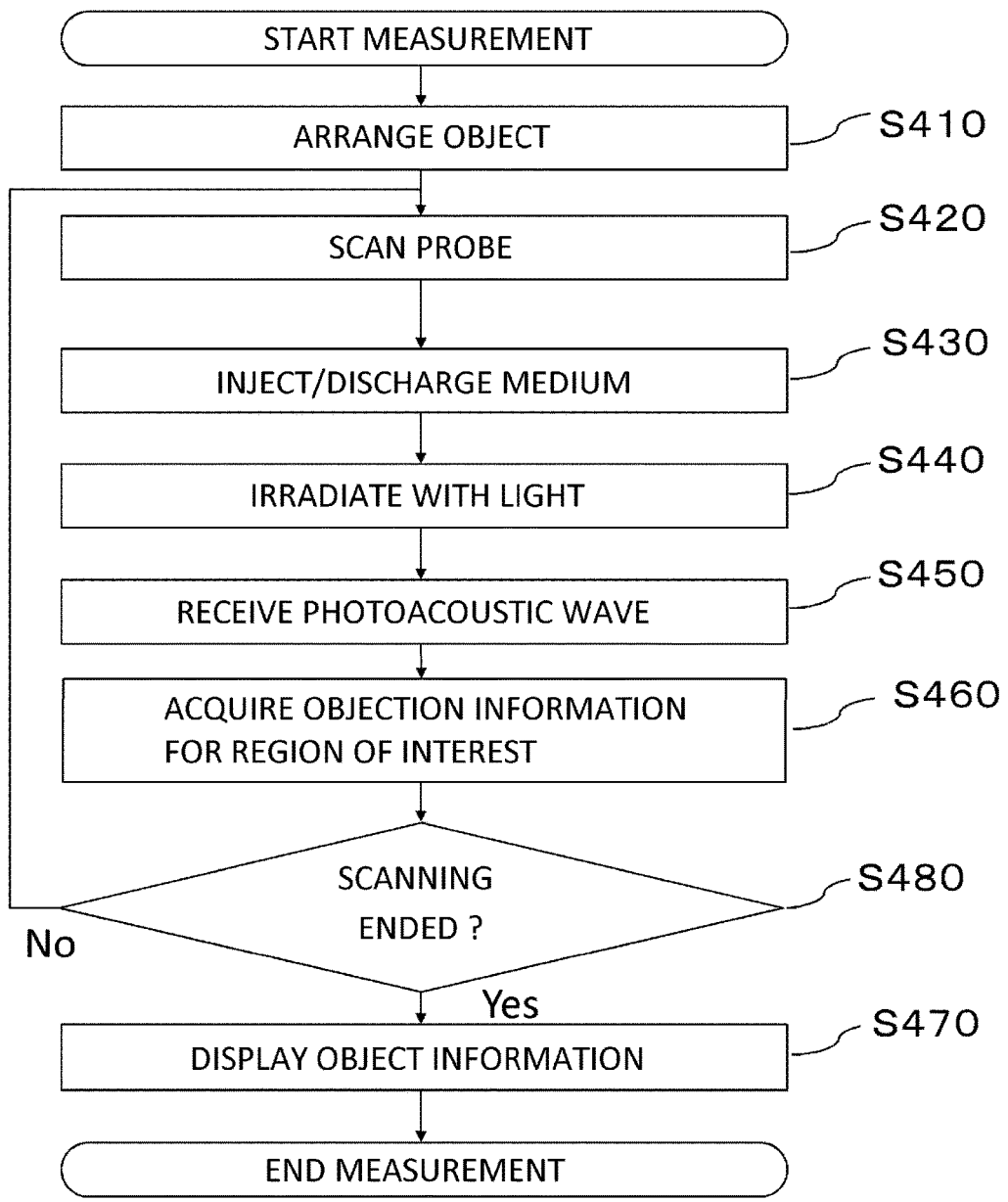
FIG. 17 is a flowchart of an object information acquiring method according to a fourth embodiment.

Next, the respective steps of the object information acquiring method relating to the present embodiment are described with reference to FIG. 17. Each step is carried out by means of the controller 130 controlling the operation of the respective constituent parts of the object information acquiring apparatus. Steps S440, S450 and S470 are similar to S120, S130 and S150 in FIG. 8, and therefore description thereof is omitted here.

(S410: Step of Arranging Object)

In this step, the object 100 is arranged in such a manner that the vicinity of the center of curvature 113 of the probe 110, which is the region of high resolution, is positioned inside the region of interest 101. The object 100 is introduced into the probe 110 so as to pass through the two apertures 111, and the positional relationship between the probe 110 and the object 100 is adjusted. After arranging the object, the trajectory for scanning the probe 110 is set by the controller 130. The setting of the trajectory may be made by an operator or may be performed automatically by the controller 130. In this case, it is possible to acquire the position or shape of the object 100 by providing a position measurement unit 705 inside the probe 110, and to use the position or shape to set the scanning trajectory.

(S420: Step of Scanning Probe)

In this step, the probe 110 is moved successively to a plurality of measurement positions on the basis of the scanning trajectory set in S410. The scanning may be performed continuously, or by a step-and-repeat method.

(S430: Step of Injecting and Discharging Medium)

In this step, the amount of medium to be injected into the individual bags 901 is adjusted on the basis of the positional relationship between the object 100 and the center of curvature 113 at each measurement position. Similarly to the second embodiment, the amount of medium injected is made smaller in bags 901 towards the side where the distance from the surface of the object 100 to the center of curvature 113 is long (deep). In this case, since the distance from the surface of the object 100 to the center of curvature 113 changes with the movement of the measurement position by the scanning action, then the pumps 902 change the injected amount of medium, in corresponding fashion. The change in the distance can be calculated for each measurement position by using the position or shape of the object 100 acquired in S410, and the set scanning trajectory. Furthermore, it is also possible to prevent the object 100 from being pressed by the bags 901 by continuously controlling the injection and discharge of medium in accordance with the scanning trajectory, aside from the measurement position.

(S460: Step of Acquiring Property Information in Region of Interest)

In this step, the reception signal acquired in S450 is used to acquire property information near the center of curvature 113, of the inside of the region of interest 101, by a similar technique to that used in the first embodiment. The property information is saved in the storage unit 132 progressively, as scanning is performed. The process ends when the entire region of interest has been scanned. The property information can finally be calculated collectively after completing scanning and the acquisition of an electrical signal in the entire region of interest.

In the determination block S480, it is determined whether or not scanning has ended. Steps S420 to S460 are repeated until reaching the end of the scanning trajectory. When the end of the scanning trajectory is reached and scanning ends, the procedure advances to S470.

Figure 18:
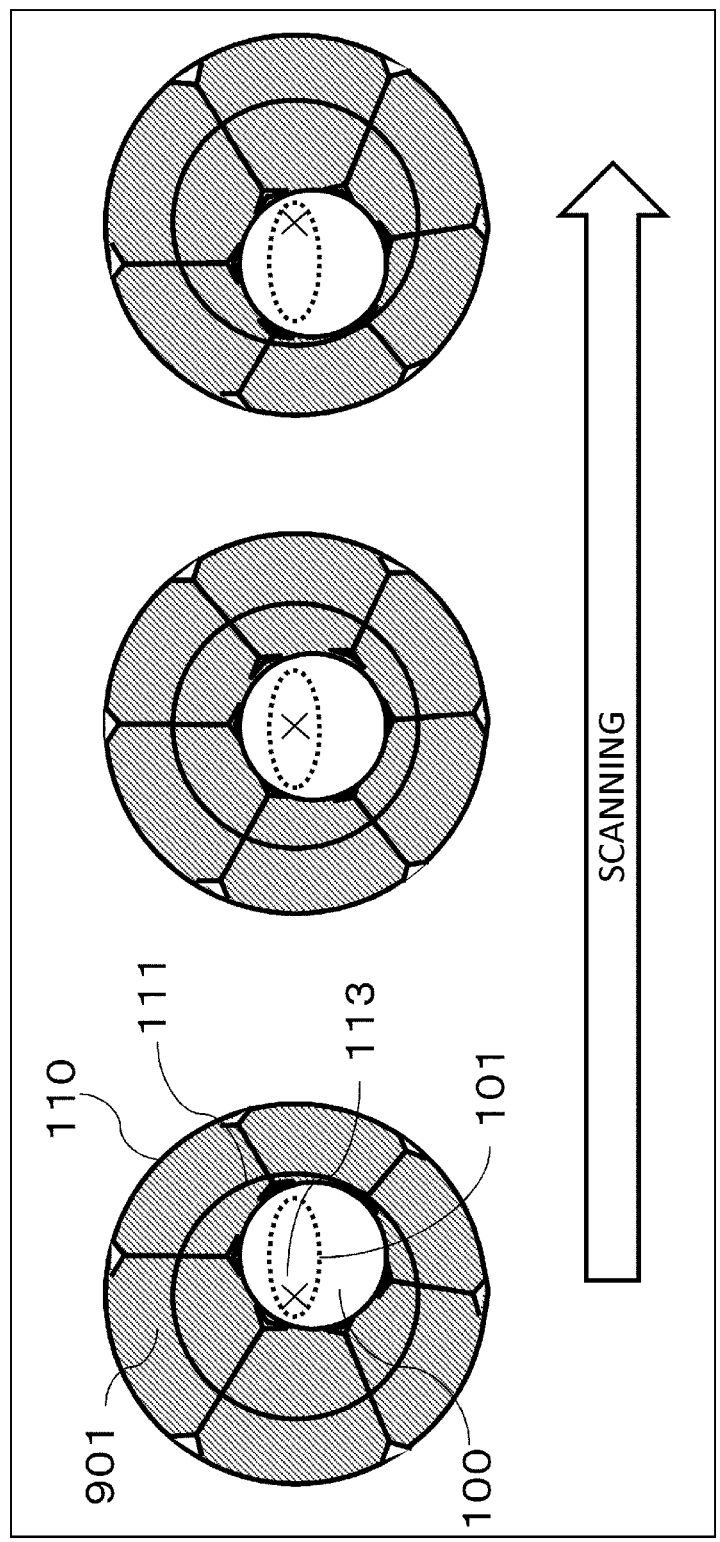
FIG. 18 is a diagram showing a relationship between scanning and the details of a plurality of bags.

In the present embodiment, by changing the amount of medium injected into the bags 901 individually for each measurement position in the scanning action, at S430, as shown in FIG. 18, then it is possible to prevent the object 100 from being pushed and moved by the bags 901. Consequently, the inside of a broad region of interest 101 can be scanned and measured in the region of high resolution near the center of curvature 113. By using a reception signal acquired in this way, it is possible to acquire property information for the entire region of interest 101, at high resolution.

Fifth Embodiment

In the present embodiment, property information for a broader region of interest can be acquired at high resolution, and with high contrast, by scanning the probe with respect to the object. In principle, the same constituent elements as the first, third and fourth embodiments are labelled with the same reference numerals and description thereof is omitted here.

<Configuration of Object Information Acquiring Apparatus>

Figure 19:
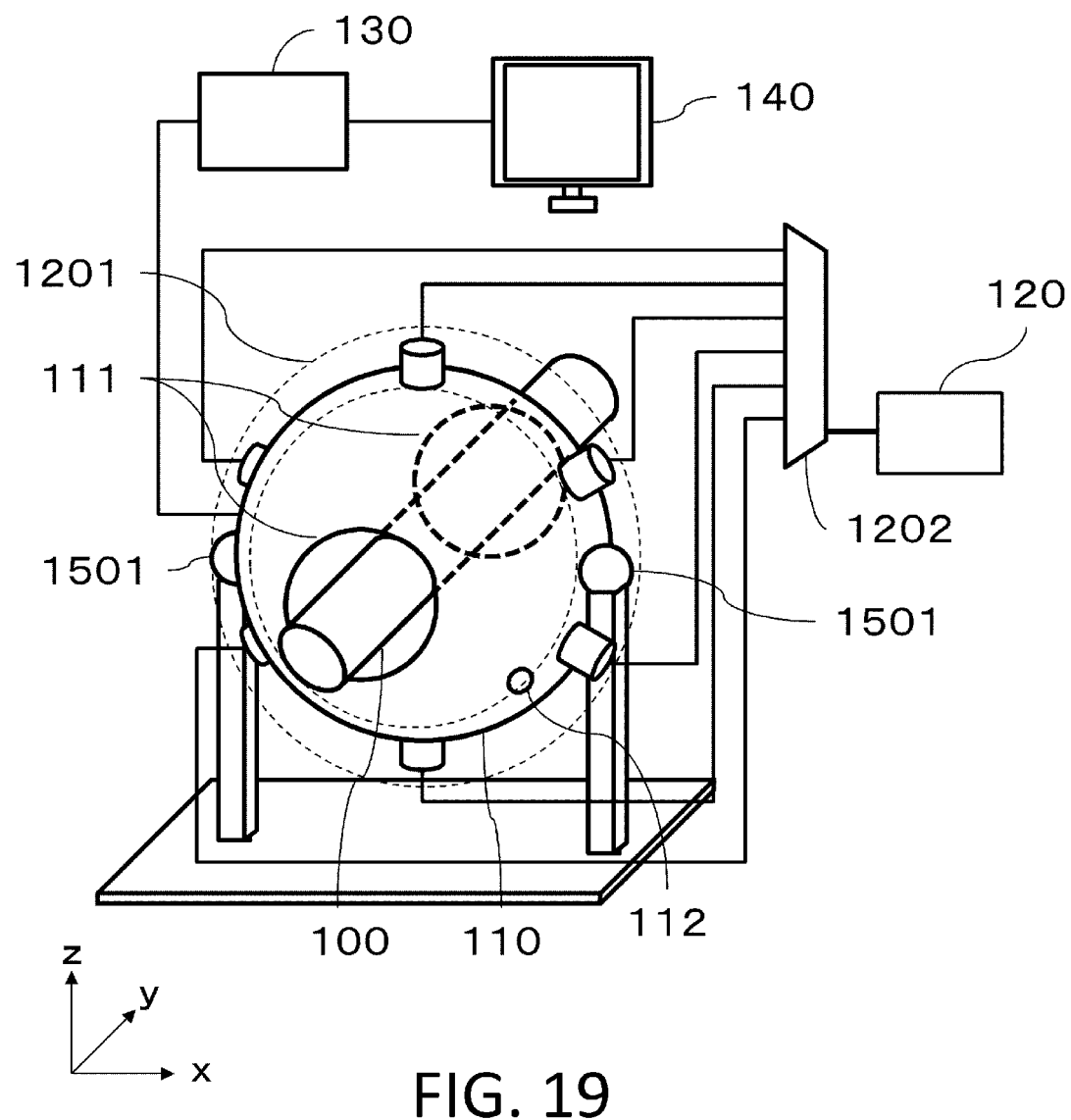
FIG. 19 is a schematic drawing of the an object information acquiring apparatus according to a fifth embodiment.

FIG. 19 is a schematic drawing of the object information acquiring apparatus according to the present embodiment, in which the probe moving section 703 shown in FIG. 7B is installed on the object information acquiring apparatus according to the third embodiment shown in FIG. 12. Similarly to the fourth embodiment, the probe 110 can perform a scanning action relative to the object 100.

<Object Information Acquiring Method>

Figure 20:
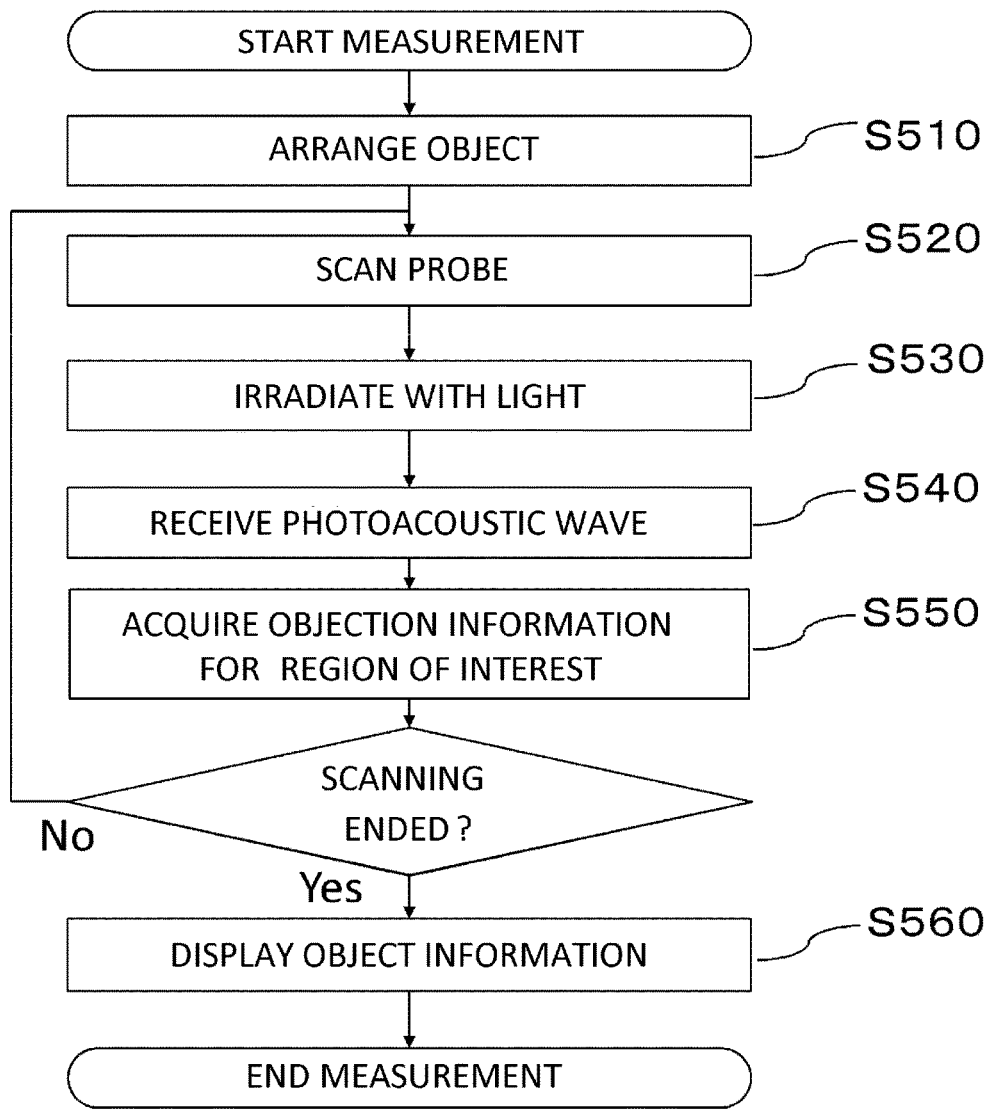
FIG. 20 is a flowchart of an object information acquiring method according to a fifth embodiment.
Figure 21:
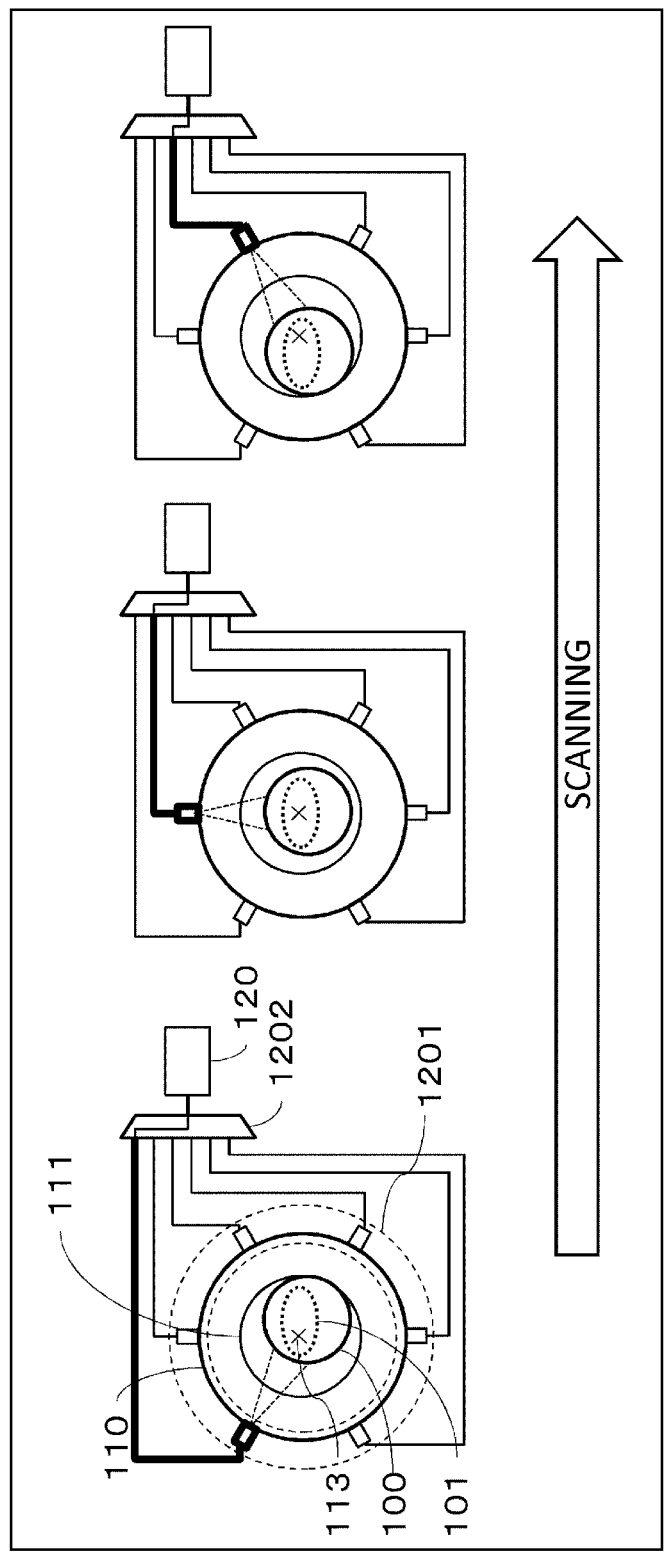
FIG. 21 is a diagram showing a relationship between scanning and the light irradiation.

Next, the respective steps of the object information acquiring method relating to the present embodiment are described with reference to FIG. 20. Each step is carried out by means of the controller 130 controlling the operation of the respective constituent parts of the object information acquiring apparatus. Steps S510, S520, S540, S550, S560 in FIG. 20 are respectively the same as S410, S420, S450, S460 and S470 in FIG. 17, and description thereof is omitted here.

(S530: Step of Generating a Photoacoustic Wave by Irradiating the Object with Light)

In this step, the object 100 is irradiated with light from an optical system 1201 selected by the switching device 1202. The light is absorbed by the inside of the object 100, and a photoacoustic wave is generated by the photoacoustic effect.

Similarly to the third embodiment, the selection of the optical system in the present embodiment is made on the basis of the positional relationship between the object 100 and the center of curvature 113 at each measurement position. In other words, the optical system 1201 situated on the side at the shorter (shallower) distance from the surface of the object 100 to the center of curvature 113 is selected. In this case, since the distance from the surface of the object 100 to the center of curvature 113 changes with the movement of the measurement position by the scanning action, then the optical system selected is also changed, in corresponding fashion. The change in the distance can be calculated for each measurement position by using the position or shape of the object 100 acquired in S510, and the set scanning trajectory. The selection of the optical system is made by the switching device 1202 in accordance with controls made by the controller 130.

In the present embodiment, the inside of a broad region of interest 101 is scanned and measured in a region of high resolution near the center of curvature 113, while in S530, the optical system 1201 which radiates light is changed for each measurement position of the scanning action, as shown in FIG. 22. Consequently, the SN ratio of the reception signal can be improved, similarly to the third embodiment. By using this reception signal, it is possible to acquire property information for the entire region of interest 101, at high resolution and with high contrast.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment (s) of the present invention, and by a method performed by the computer of the system or apparatus by, for example, reading out and executing the computer executable instructions from the storage medium to perform the functions of one or more of the above-described embodiment (s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-262967, filed on Dec. 25, 2014, which is hereby incorporated by reference herein in its entirety.

What is claimed is:

1. An apparatus comprising:
an irradiator configured to irradiate an object with light;
a probe including a plurality of transducers, configured to output a reception signal by receiving an acoustic wave generated from the object irradiated with the light, and a housing which surrounds the plurality of transducers,
a plurality of bags arranged inside the housing, each of the plurality of bags being made from a material that is expandable and contractible,
a medium supplier configured to supply a matching medium for propagating the acoustic wave into each of the plurality of bags in such a manner that the acoustic wave propagates between the object and the plurality of transducers via the matching medium, and
a controller configured to acquire property information on a region of interest of the object by using the reception signal,
wherein the plurality of transducers are arranged on an internal surface of the housing as a transducer arrangement surface,
wherein the internal surface of the housing has a spherical surface shape such that a region of high resolution is formed inside the housing,
wherein the controller controls an amount of the matching medium supplied to each of the plurality of bags in such a manner that the region of high resolution is included in the region of interest of the object, and
wherein the housing has a plurality of apertures through which the object passes in such a manner that the irradiator irradiates the object with the light and the plurality of transducers receives the acoustic wave while the object passes through the plurality of apertures and is held by the plurality of bags when the matching medium is supplied.

2. The apparatus according to claim 1, wherein the irradiator is capable of irradiating a plurality of positions on the object with the light; and
the controller selects the position on the object for irradiating from among the plurality of positions, on the basis of a distance between the surface of the object and the region of high resolution.

3. The apparatus according to claim 1, further comprising a mover configured to move the probe to a plurality of measurement positions, wherein the controller changes the amount of the matching medium supplied to each of the plurality of bags for each of the plurality of measurement positions.

4. The apparatus according to claim 1, wherein the plurality of apertures includes two apertures arranged at opposing positions on the internal surface of the housing.

5. The apparatus according to claim 1, wherein the object has a lengthwise direction, and
the plurality of apertures are arranged such that the lengthwise direction of the object passes through the plurality of apertures.

6. The apparatus according to claim 1, further comprising a holding unit configured to hold the object, wherein the holding unit is arranged on the outside of the probe.

7. The apparatus according to claim 6, wherein the holding unit is arranged corresponding to each of the plurality of apertures.

8. The apparatus according to claim 1, further comprising a position measurement unit configured to measure a position of the object, wherein the position measurement unit is arranged inside the housing.

9. The apparatus according to claim 8, wherein the position measurement unit is a camera, a laser displacement meter, or a laser shape measurement device.

10. The apparatus according to claim 1, further comprising a plurality of cameras arranged such that optical axes of each of the plurality of cameras converge on the region of high resolution.

11. The apparatus according to claim 1, wherein a directivity axis of each of the plurality of transducers directs towards an inside of the housing.

12. The apparatus according to claim 1, wherein the plurality of apertures are arranged such that a part of the object is positioned at an inside of the housing by passing the object through the plurality of apertures.

13. The apparatus according to claim 1, further comprising a hinge configured to split the housing.

14. The apparatus according to claim 1, wherein the region of high resolution includes a position where a directivity axis of each of the plurality of transducers directs.

15. An apparatus comprising:
an irradiator configured to irradiate an object with light;
a probe including a plurality of transducers configured to output a reception signal by receiving an acoustic wave generated from the object irradiated with the light, and a housing which surrounds the plurality of transducers, and
a controller configured to acquire property information on a region of interest of the object by using the reception signal, wherein the plurality of transducers are arranged on an internal surface of the housing as a transducer arrangement surface, wherein the housing has a spherical surface shape in such a manner that a region of high resolution is formed inside the housing, and wherein the housing has a plurality of apertures through which the object passes in such a manner that the irradiator irradiates the object with the light and the plurality of transducers receive the acoustic wave while the object passes through the plurality of apertures and the region of high resolution is included in the region of interest of the object.

* * * * *